United States Patent
Nghiem et al.

(10) Patent No.: US 7,289,855 B2
(45) Date of Patent: Oct. 30, 2007

(54) IMPLANTABLE MEDICAL DEVICE PACKAGE ANTENNA

(75) Inventors: David Nghiem, Fridley, MN (US); Lawrence A. Baylis, Fridley, MN (US); David B. Bohn, Ham Lake, MN (US); Glenn R. Biddick, Minneapolis, MN (US); John J Spitzley, Hudson, WI (US); Len D. Twetan, Excelsior, MN (US)

(73) Assignee: Medtronic, Inc., Minneapolis, MN (US)

( * ) Notice: Subject to any disclaimer, the term of this patent is extended or adjusted under 35 U.S.C. 154(b) by 202 days.

(21) Appl. No.: 10/864,704

(22) Filed: Jun. 9, 2004

(65) Prior Publication Data

US 2006/0020300 A1    Jan. 26, 2006

(51) Int. Cl.
*A61N 1/00* (2006.01)
*A61B 19/00* (2006.01)

(52) U.S. Cl. .............................. 607/60; 607/9; 607/27; 607/30; 607/32; 607/156; 128/899; 128/897

(58) Field of Classification Search ................ 607/156, 607/30, 32, 36, 60, 9, 27; 128/903, 897–9, 128/899
See application file for complete search history.

(56) References Cited

U.S. PATENT DOCUMENTS

| | | | |
|---|---|---|---|
| 3,774,110 A * | 11/1973 | Roveti ........................ 324/133 |
| 4,441,498 A * | 4/1984 | Nordling ..................... 607/32 |
| 4,542,532 A | 9/1985 | McQuilkin ................... 455/78 |
| 5,113,869 A | 5/1992 | Nappholz et al. ........... 128/696 |
| 5,345,362 A | 9/1994 | Winkler ....................... 361/681 |
| 5,404,877 A | 4/1995 | Nolan et al. ................. 128/671 |
| 5,697,958 A | 12/1997 | Paul et al. ..................... 607/31 |
| 5,720,770 A | 2/1998 | Nappholz et al. ............. 607/30 |
| 5,766,232 A | 6/1998 | Grevious et al. ............. 607/60 |
| 5,861,019 A | 1/1999 | Sun et al. ..................... 607/60 |
| 6,009,350 A * | 12/1999 | Renken ......................... 607/32 |
| 6,167,312 A * | 12/2000 | Goedeke ....................... 607/60 |
| 6,240,317 B1 | 5/2001 | Villaseca et al. ............. 607/60 |
| 6,456,256 B1 * | 9/2002 | Amundson et al. ......... 343/873 |
| 6,482,154 B1 | 11/2002 | Haubrich et al. ........... 600/300 |
| 7,005,968 B1 * | 2/2006 | Bridgelall ................ 340/10.42 |
| 7,096,068 B2 * | 8/2006 | Mass et al. ................... 607/32 |

\* cited by examiner

*Primary Examiner*—Carl Layno
*Assistant Examiner*—Natasha Patel
(74) *Attorney, Agent, or Firm*—Michael C. Soldner

(57) ABSTRACT

A wireless communication system is provided that includes an antenna structure adapted for coupling to a medical device antenna when the medical device is not implanted in a patient's body. The antenna structure effectively extends the medical device antenna length, thereby improving the efficiency and reliability of a communication link between the medical device and a programmer or monitor outside the implanted environment. The antenna structure is fabricated from any conductive material, which may be in the form of conductive wire, tape, ink, foil, film, adhesive or the like, and is attached to a portion of a medical device packaging assembly or another accessory device or substrate such as a pouch or overlay. The antenna structure may be a monopole, dipole, slot antenna, microstrip patch, or loop antenna, and may be fixed or movable relative to the substrate on which it is implemented.

14 Claims, 20 Drawing Sheets

IMPLANTABLE MEDICAL DEVICE PACKAGE ANTENNA

FIELD OF THE INVENTION

The present invention relates generally to medical devices and in particular to a wireless communication system for use with a medical device that includes an antenna structure adapted for coupling to a medical device antenna for use in communication operations performed outside an implanted environment.

BACKGROUND OF THE INVENTION

In the context of implantable medical devices, it has become common to provide a communication link between the implanted device and an external programmer or monitor in order to allow for transmission of commands from the external device to the implanted device and to allow for transmission of stored information and/or sensed physiological parameters from the implanted device to the external programmer. Conventionally, communication between an implanted device and an external programmer has been accomplished by means of a telemetry system which includes transceivers located within the implanted medical device and in an external programmer or monitor, each having a radio transmitter/receiver and one or more antennas.

The implanted device typically includes an antenna located either within the hermetic device housing containing the circuitry, as disclosed in U.S. Pat. No. 4,542,532 issued to McQuilkin, in a plastic header or connector block used to interconnect the device to electrical leads as disclosed in U.S. Pat. No. 5,697,958 issued to Paul et al., or mounted to the device housing as in U.S. Pat. No. 5,861,019 issued to Sun et al., and U.S. Pat. No. 5,720,770 issued to Nappholz et al., all incorporated herein in their entireties. In the past, the programmer or monitor has been provided with a programming head containing an antenna, intended to be placed on or near the patient's body in close proximity to the implanted device. The programming head may be coupled to the external programmer or monitor by means of a cord, as disclosed in U.S. Pat. No. 5,766,232 issued to Grevious et al. The physician handling the programming head has various tasks to perform and positioning of the programming head to a particular location and maintaining that position to maximize received telemetry signal strength is a task that sometimes makes completing the telemetry functions cumbersome. In particular, during an implantation procedure when the IMD is located within a sterile surgical field, the task of positioning of the programming head over the device without breaching the sterile field can become awkward.

Recently, communication systems for implantable medical devices have been proposed in which the programming head is done away with. Communication occurs directly between the programmer or monitor, which may be located some distance from the patient, and the implanted medical device. Such systems are disclosed in U.S. Pat. No. 5,404,877 issued to Nolan et al, U.S. Pat. No. 5,113,869 issued to Nappholz, U.S. Pat. No. 6,240,317 issued to Villaseca et al., and U.S. Pat. No. 6,482,154 issued to Haubrich et al., all of which patents are hereby incorporated herein by reference in their entireties. Long-range telemetry systems, which do not require a programming head to be placed over the IMD, simplify a caregiver's task in programming an IMD, particularly in a crowded clinical, operating room or sterile environment.

Medical device telemetry systems are generally designed for maximum efficiency under implanted conditions, i.e. the dielectric constant and conductivity of human tissue is taken into account when designing the telemetry and antenna system. Programming and interrogation operations, however, are not limited to occurring after device implant. During an implant procedure, telemetry communication may be required for testing procedures or for verifying or customizing initial programmable parameter values before the IMD is implanted. The surgical theater can have multiple RF interferences including other monitoring and medical equipment and RF barriers such as stainless steel surgical carts. These interferences and barriers may make long-range telemetry systems, which have been optimized for operation in the implanted environment, less efficient and reliable when used prior to IMD implantation. An IMD telemetry system is needed, therefore, which takes advantage of the elimination of a programming head but still produces consistently reliable and efficient telemetry transmissions regardless of the operating environment.

BRIEF SUMMARY OF THE INVENTION

The present invention provides a telemetry system for an implantable medical device (IMD) that includes a package antenna adapted for coupling to the IMD antenna when the IMD is outside the implanted environment. The package antenna effectively extends the IMD antenna length prior to implantation of the IMD, thereby improving the efficiency and reliability of a telemetry link between the IMD and a programmer or monitor prior to IMD implantation. The package antenna may be fabricated from any conductive material in the form of conductive wire, tape, ink, foil, film, adhesive or the like, applied to a portion of an IMD packaging assembly or another accessory device or substrate such as a pouch or overlay. The package antenna is selected to withstand sterilization procedures such that it may be used within a sterile surgical field.

The package antenna may be adapted for capacitive coupling or direct electrical coupling to the IMD antenna. The package antenna may be provided in a variety of forms, including but not limited to a monopole, dipole, loop, microstrip patch, or slot antenna. In some embodiments the package antenna is fixed relative to the packaging tray assembly, pouch, overlay or other substrate on which the package antenna is located. In other embodiments, the package antenna may be movable, for example, such as a folding or telescoping antenna. The package antenna promotes consistently efficient and reliable telemetry communication between an IMD and a programmer or monitor, regardless of the telemetry environment.

DETAILED DESCRIPTION OF THE PREFERRED EMBODIMENTS

The present invention is directed toward providing a wireless communication system for use with medical devices which includes an antenna structure for extending the effective length of a medical device antenna. The present invention may be practiced in conjunction with an external or implantable medical device system for improving the communication range and efficiency of a wireless communication transmission between the medical device and another medical device, a programmer or monitor. For exemplary illustration, the embodiments described herein relate to an implantable medical device system wherein an antenna structure improves the reliability and efficiency of wireless communication prior to implantation of the IMD.

Figure 1:
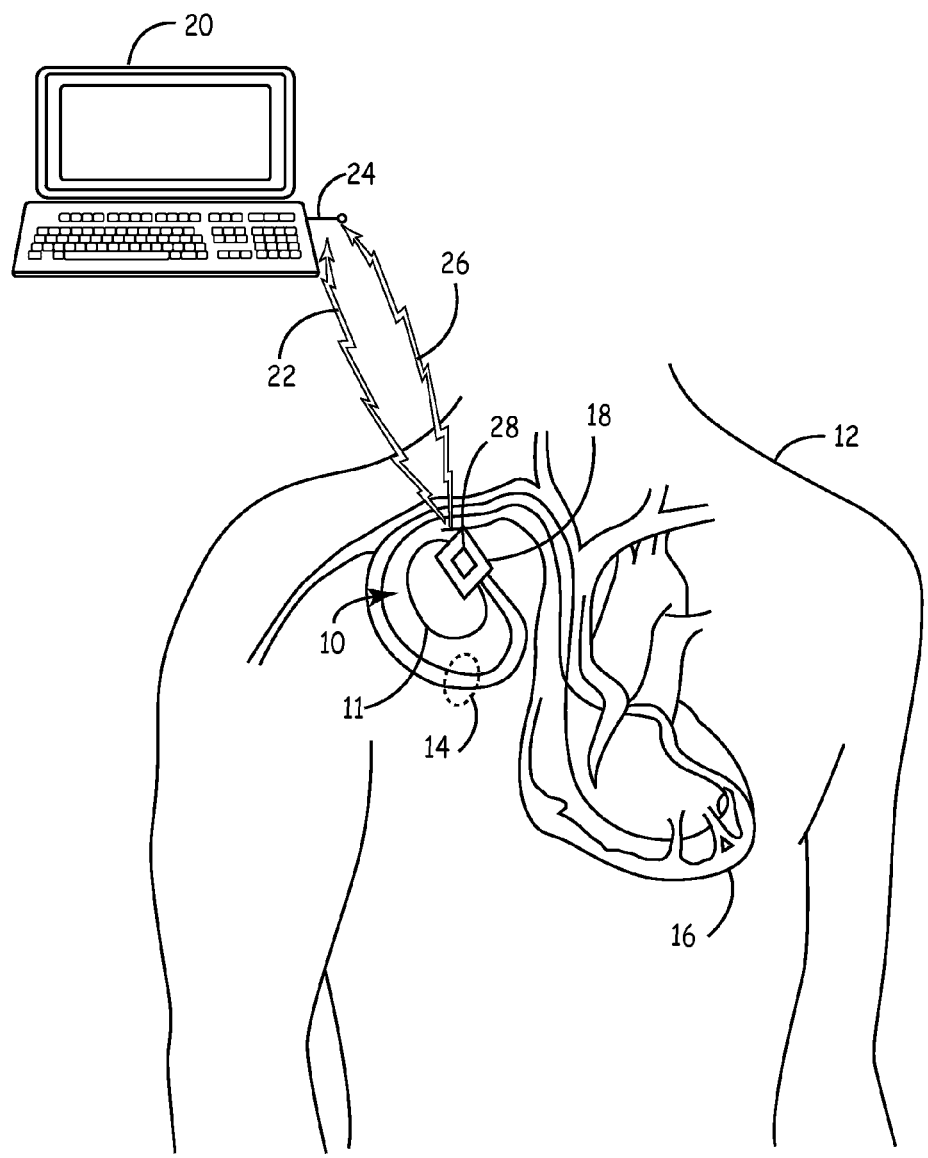
FIG. 1 is a schematic diagram of an IMD system shown after implantation.

FIG. 1 is a schematic diagram of an IMD system shown after implantation. An IMD 10 is implanted in a patient 12 beneath the patient's skin or muscle and, in this example, is electrically coupled to the heart 16 of the patient 12 through pace/sense electrodes and lead conductor(s) of one or more associated cardiac pacing leads 14 in a manner known in the art. IMD 10 is capable of telemetric communication with an external medical device (EMD) 20, typically embodied as a programmer or monitor. For exemplary illustration, IMD 10 is shown here as a programmable cardiac stimulation device. However numerous types of IMDs exist with which the present invention may be practiced including implantable drug pumps, implantable neuromuscular stimulators, physiological monitors, or other IMDs that are capable of performing telemetry communications with an EMD.

Programming commands or data are transmitted between an IMD RF telemetry antenna 28 and an external RF telemetry antenna 24 associated with the external programmer 20. In this case, it is not necessary that the external RF telemetry antenna 24 be contained in a programmer RF head so that it can be located close to the patient's skin overlying the IMD 10. Instead, the external RF telemetry antenna 24 can be located on the case of the external programmer 20, and the programmer 20 can be located some distance away from the patient 12. For example, the external programmer 20 and external RF telemetry antenna 24 may be on a stand a few meters or so away from the patient 12.

In an uplink telemetry transmission 22, the external RF telemetry antenna 24 operates as a telemetry receiver antenna, and the IMD RF telemetry antenna 28 operates as a telemetry transmitter antenna. Conversely, in a downlink telemetry transmission 26, the external RF telemetry antenna 24 operates as a telemetry transmitter antenna, and the IMD RF telemetry antenna 28 operates as a telemetry receiver antenna. Both RF telemetry antennas are coupled to transceiver circuitry including a transmitter and a receiver.

IMD RF telemetry antenna 28 is generally designed for efficient, reliable telemetry transmission in the implanted environment. IMD RF telemetry antenna 28 may be located within the hermetic IMD housing 11 containing the device circuitry, in or on a plastic header or connector block 18 used to interconnect the IMD 10 to electrical leads 14, mounted to the IMD housing 11, or incorporated as a portion of one of the electrical leads 14, as generally described in the above-incorporated references. When located outside the IMD housing 11, IMD RF telemetry antenna 28 is coupled to RF transceiver circuitry within the housing 11 of IMD 10 via an insulated, conductive feed-through extending through the connector block 18. IMD RF telemetry antenna 28 is typically a monopole antenna having a length tuned to function optimally at the radio frequencies chosen for use in the telemetry system.

Figure 2:
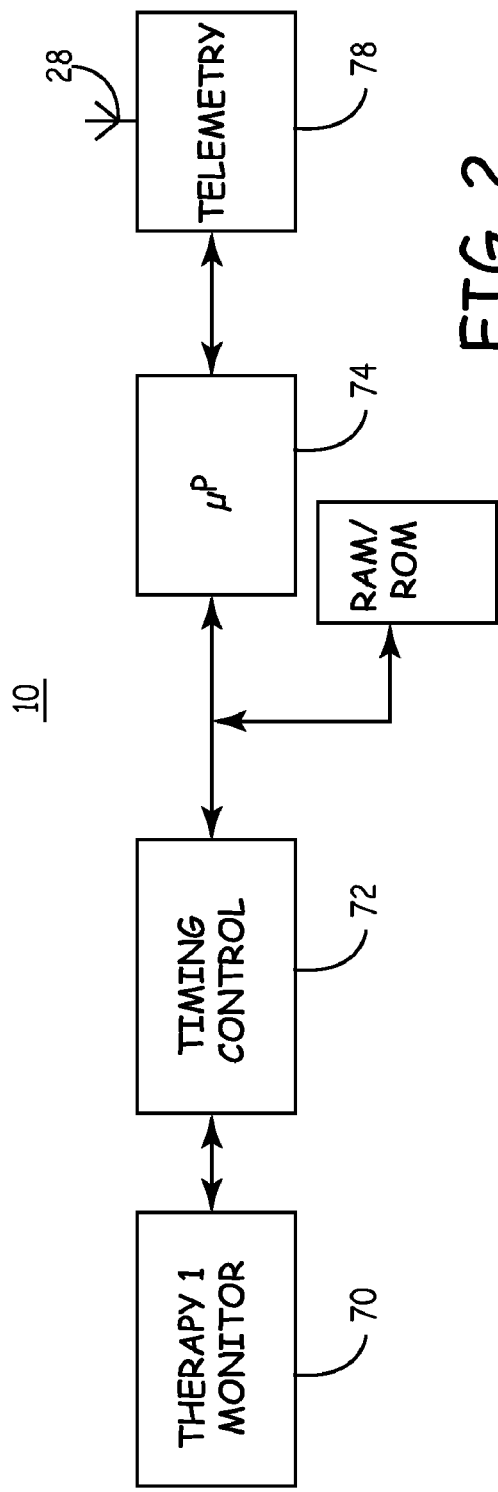
FIG. 2 illustrates typical components of the IMD shown in FIG. 1.

FIG. 2 illustrates typical components of IMD 10 shown in FIG. 1. Major operative structures common to IMD 10 are represented in a generic format. IMD 10 contains timing and control circuitry 72 and an operating system that may employ microprocessor 74 or a digital state machine for timing, sensing and pacing functions in accordance with a programmed operating mode. IMD 10 also contains therapy/monitor 70 which may include sense amplifiers for detecting cardiac signals, patient activity sensors or other physiologic sensors for sensing the need for cardiac output, and pulse generating output circuits for delivering pacing pulses to at least one chamber of heart 16 (see FIG. 1) under control of the operating system in a manner well known in the prior art.

The operating system includes memory registers or RAM/ROM 76 for storing a variety of programmed-in operating mode and parameter values that are used by the operating system. The memory registers or RAM/ROM 76 may also be used for storing data compiled from sensed physiologic activity and/or relating to device operating history for telemetry out on receipt of a retrieval or interrogation instruction. All of these functions and operations are well known in the art, and many are generally employed to store operating commands and data for controlling device operation and for later retrieval to diagnose device function or patient condition.

Programming commands or data are received by or transmitted from telemetry circuitry 28 through IMD RF telemetry antenna 28. Telemetry circuitry 78 includes a transceiver having both a telemetry transmitter and telemetry receiver. The telemetry circuitry 28 in IMD 10 is coupled to control circuitry and registers operated under the control of microcomputer 74.

Figure 3:
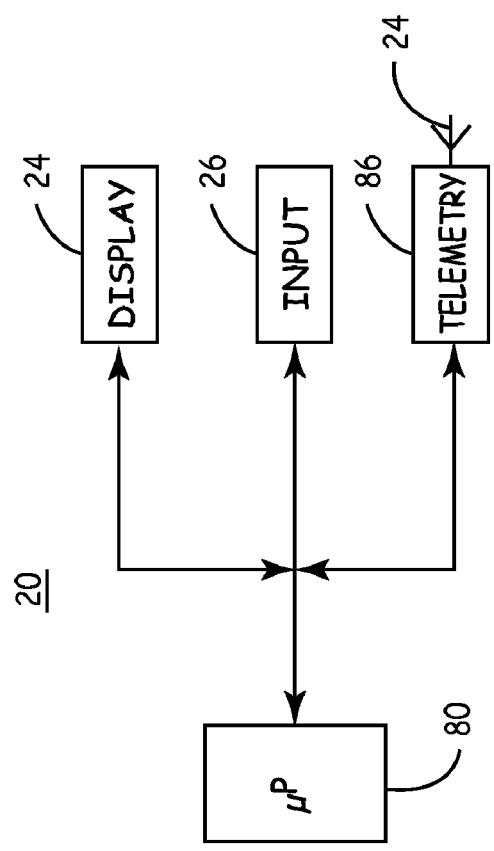
FIG. 3 is a simplified block diagram of major functional components typically included in an external medical device embodied as a programmer or monitor, such as the external medical device shown in FIG. 1.

FIG. 3 is a simplified block diagram of major functional components typically included in an EMD, such as EMD 20 shown in FIG. 1. The external RF telemetry antenna 24 on EMD 20 is coupled to a telemetry transceiver 86, which includes an antenna driver circuit board having a telemetry transmitter and telemetry receiver. The telemetry transmitter and telemetry receiver are coupled to control circuitry and registers operated under the control of microcomputer 80.

EMD 22 may be a personal computer type, microprocessor-based device incorporating a central processing unit 80, which may be, for example, an Intel Pentium microprocessor or the like. A system bus interconnects CPU 80 with a hard disk drive, storing operational programs and data, and with a graphics circuit and an interface controller module. A floppy disk drive or a CD ROM drive may also be coupled to the bus and is accessible via a disk insertion slot within the housing of EMD 20. EMD 20 may include solid-state memory for long-term storage of data.

In order for the physician, patient, or other caregiver or authorized operator to interact with the EMD 20, a keyboard or other user interface input 26 coupled to CPU 80 is optionally provided. However the primary communications mode may be through graphics display screen of the well-known "touch sensitive" type controlled by a graphics circuit. A user of EMD 20 may interact therewith through the use of a stylus, also coupled to a graphics circuit, which is used to point to various locations on screen or display 24, which display menu choices for selection by the user or an alphanumeric keyboard for entering text or numbers and other symbols. Various touch-screen assemblies are known and commercially available.

Display 24 and/or the user interface 26 allow a user to enter command signals to initiate transmissions of downlink or uplink telemetry and to initiate and control telemetry sessions once a telemetry link with an implanted device has been established. Other types of user interaction mechanisms and electronics may be implemented such as voice recognition/response systems.

Display screen 24 is also used to display patient related data, menu choices and data entry fields used in entering the data or messages alerting a patient or user to pertinent programming or monitoring conditions. Display screen 24 also displays a variety of screens of telemetered out data or real time data. Display screen 24 may also display uplinked event signals as they are received and thereby serve as a means for enabling the user to timely review IMD operating history and status.

EMD 20 may also include an interface module, which includes a digital circuit, non-isolated analog circuit, and/or isolated analog circuit for coupling peripheral or accessory devices or instruments to EMD 20. The digital circuit enables the interface module to communicate with the interface controller module. For example, EMD 20 may be provided with a strip chart printer or the like coupled to interface controller module so that a hard copy of a physiological signals or graphics displayed on the display screen can be generated. EMD 20 may be embodied or include features as generally disclosed in U.S. Pat. No. 5,345,362 issued to Winkler, which is incorporated herein by reference in its entirety.

Figure 4:
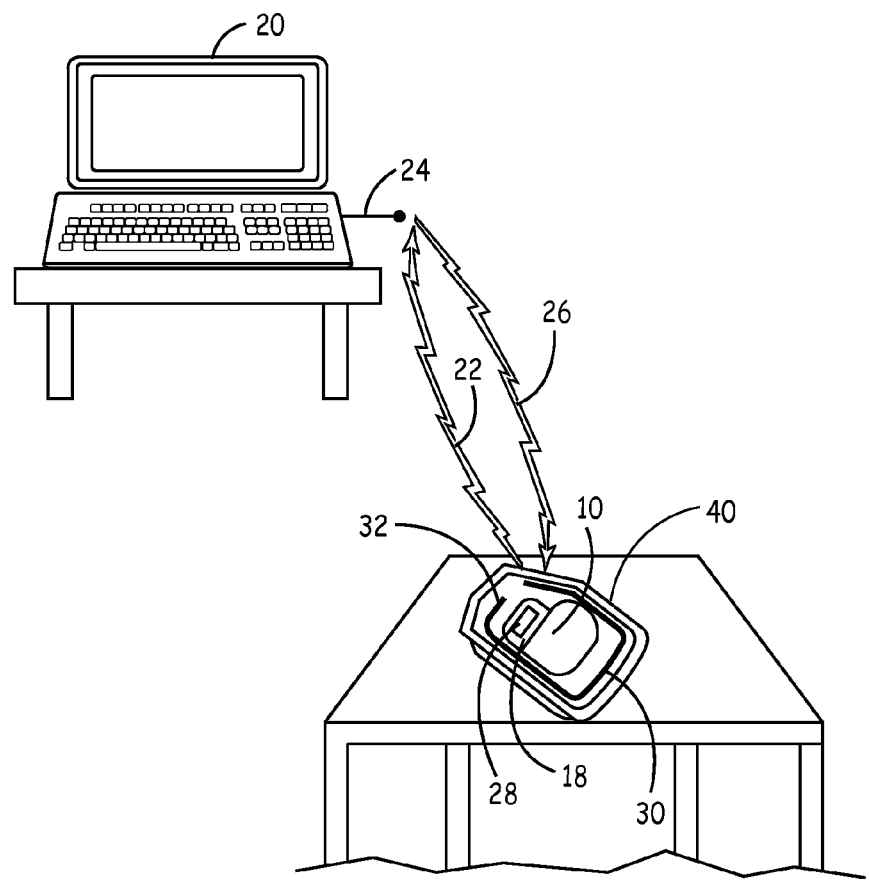
FIG. 4 is a schematic diagram of an IMD system shown prior to implantation including a package antenna in accordance with the present invention.

FIG. 4 is a schematic diagram of an IMD system shown prior to implantation. Prior to implantation, IMD 10 may remain contained within a packaging tray 40, which is typically sterilized with IMD 10 inside such that it may be "dropped" into a sterile operating environment from non-sterile outer packaging material. EMD 20 may be located some distance away, for example a few meters, within the surgical theater.

In accordance with the present invention, a package antenna 30 is provided such that it may be coupled to IMD RF antenna 28 prior to IMD 10 implantation to allow efficient telemetry communication between IMD 10 and EMD 20. As will be described in greater detail below, package antenna 30 may be located on packaging tray 40 or an associated tray lid or on a separate pouch or overlay. The term "package antenna" is used herein to refer to an antenna used to effectively extend the length of an IMD antenna when the IMD not implanted in a patient's body. It is expected that, for convenience, such an antenna will typically be included in a package containing a sterilized IMD and is therefore referred to herein as a "package antenna." However, the use of this term is not intended to exclude antenna structures that are to be used with an IMD prior to implantation or after explantation and are packaged or provided separately from the IMD with which it will be used.

One end 32 of package antenna 30 is adapted to be coupled to IMD RF antenna 28, either directly or capacitively. Downlink telemetry link 22 and uplink telemetry link 26 may then be established between EMD RF antenna 24 and package antenna 30, which transmits the RF signals to/from IMD RF antenna 28. IMD RF antenna 28 thus acts as a transmission line when coupled to package antenna 30 during telemetry sessions performed prior to IMD implantation (or after explantation).

Package antenna 30 is fabricated from any appropriate conductive material that is selected to withstand sterilization methods used to sterilize IMD 10. The conductive material used to fabricate package antenna 30 may be in the form of a conductive wire, tape, ink, foil, film, or adhesive. Package antenna 30 is designed to provide a significant increase in antenna gain, increase in power efficiency, and improved telemetry link performance prior to implantation of IMD 10. Outside of the implanted environment, the IMD RF antenna 28 has small electrical length and acts as a transmission line instead of an efficient antenna.

Package antenna 30 is provided with a length proportional to the wavelength of the RF frequency chosen for use in the telemetry system so that it functions as an efficient antenna prior to implantation of IMD 10. In one embodiment, package antenna 30 is provided with an electrical length greater than or equal to one-fourth the RF transmission wavelength. IMD RF antenna 28, when coupled to package antenna 30, functions as a transmission line to transfer energy received/transmitted by package antenna 30 to/from telemetry circuitry enclosed in IMD 10.

Package antenna 30 may be provided as a continuous structure as shown in FIG. 4. Alternatively, package antenna 30 may be provided as two or more physically discontinuous structures located relative to each other such that capacitive coupling is established between each physically discontinuous portion to allow continuous RF energy transmission along the length of package antenna 30.

Figure 5A:
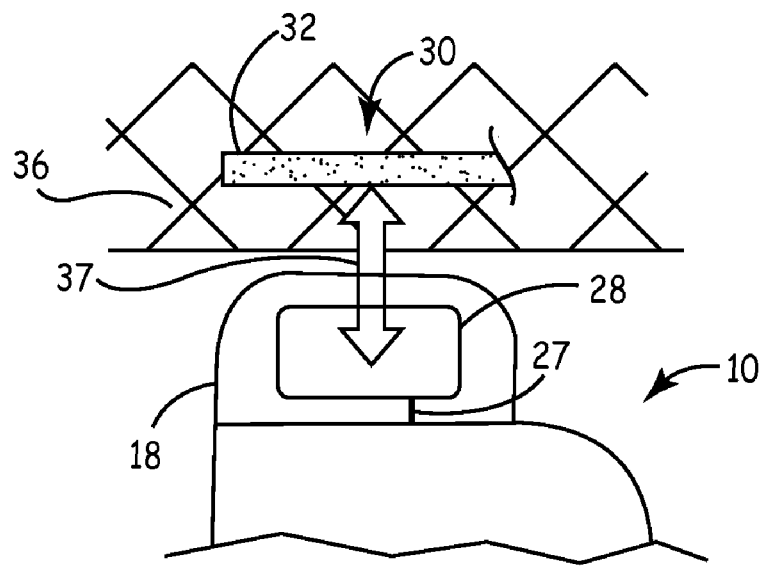
FIG. 5A is a schematic diagram illustrating capacitive coupling between a package antenna and an IMD RF antenna.

FIG. 5A is a schematic diagram illustrating capacitive coupling between package antenna 30 and IMD RF antenna 28. In some embodiments of the present invention, package antenna 30 is adapted for capacitive coupling to IMD RF antenna 28. Capacitive coupling is achieved by positioning coupling end 32 of package antenna 30 in close proximity to IMD RF antenna 28. The optimal coupling distance will depend on the application frequencies. In one embodiment, in which frequencies ranging from about 401 MHz to about 406 MHz are used, the capacitive coupling distance between coupling end 32 and the IMD RF antenna 28 should be approximately 2 mm or less. However, less efficient coupling can be achieved at greater distances if a decrease in antenna gain is desired within the wireless communication system.

The dimensions and configuration of coupling end 32 will be based on the size of IMD 10, the IMD RF antenna 28 configuration, and the desired transmission efficiency provided by package antenna 30. Coupling end 32 is shown here as having a generally circular shape of a particular size relative to IMD 10 but is illustrative of only one possible configuration for establishing capacitive coupling between end 32 and IMD RF antenna 28. Numerous coupling end configurations will be possible for use with various IMD wireless communication systems.

Package antenna 30 may be mounted or printed on a substrate 36, which may be a portion of a packaging tray or tray lid, pouch or overlay. Upon placing IMD 10 into a packaging tray or pouch or placing a tray lid or other overlay over IMD 10, package antenna 30 is located within some maximum effective distance from IMD RF antenna 28 that establishes capacitive coupling between package antenna 30 and IMD RF antenna 28 as represented by dashed arrow 37. IMD RF antenna 28 is shown located in connector block 18. As such, a feed-through 27 is provided to establish connection to transceiver circuitry enclosed in IMD 10. Package antenna 30 is removed from the telemetry system upon IMD implantation by simply removing IMD 10 from the packaging tray, pouch, overlay or other substrate 36 on which package antenna 30 is located.

Figure 5B:
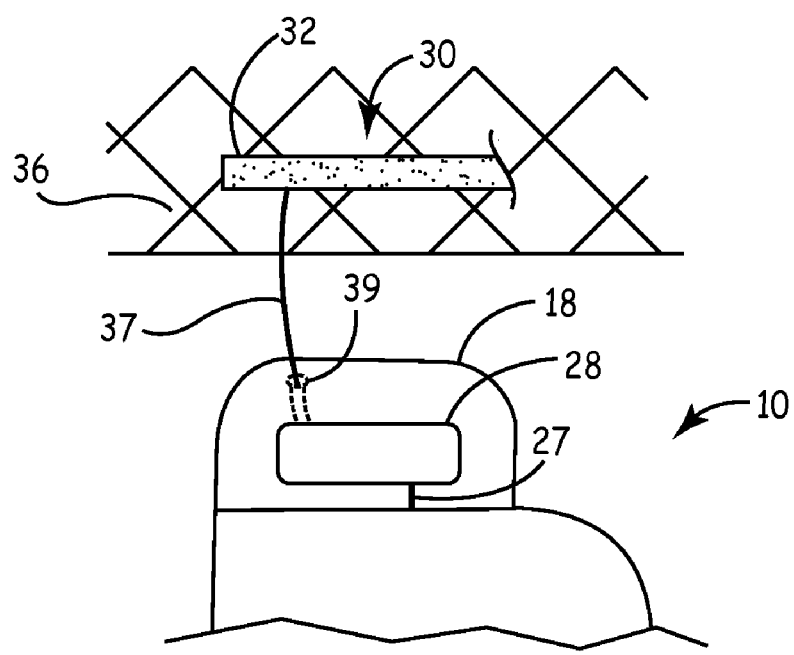
FIG. 5B is a schematic diagram illustrating direct coupling between a package antenna and an IMD RF antenna.

FIG. 5B is a schematic diagram illustrating direct coupling between package antenna 30 and IMD RF antenna 28. In some embodiments package antenna 30 is adapted for direct coupling to IMD RF antenna 28 by providing an insulated conductor 38 extending through an opening 39 of connector block 18. One end of insulated conductor 38 is electrically coupled to package antenna 30 at or near end 32. Insulated conductor 38 is electrically coupled at its other end to IMD RF antenna 28. Alternatively, insulated conductor 38 may be electrically coupled to feed-through 27 or may even be directly coupled via a dedicated feed-through to transceiver circuitry contained in IMD 10. Upon implantation, package antenna 30 is removed from the telemetry system by disconnecting insulated conductor 38. In order to protect the integrity of IMD 10 circuitry from the ingress of bodily fluids, opening 39 would be sealed prior to implantation using an appropriately sized plug or a biomedical grade sealant such as silicone glue.

Figure 6:
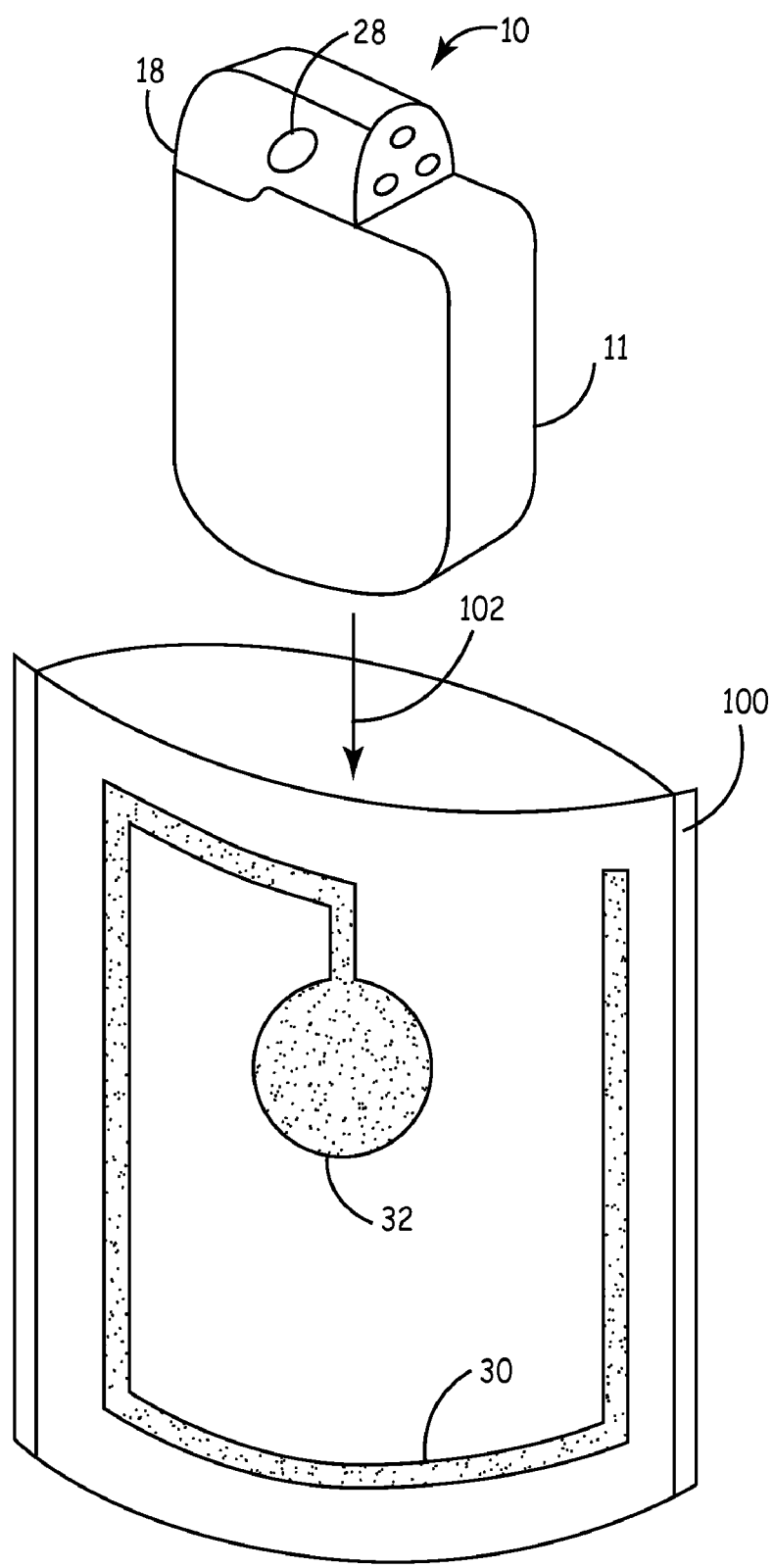
FIG. 6 is an illustration of one embodiment of a package antenna provided on a pouch in which an IMD may be placed when telemetry functions are required prior to IMD implantation or after explantation.

FIG. 6 is an illustration of one embodiment of a package antenna wherein package antenna 30 is located on a pouch 100 in which IMD 10 may be placed when telemetry functions are required prior to implant or after explant. Pouch 100 will typically be formed from a plastic, non-conductive material that preferably withstands sterilization methods used to sterilize IMD 10. Pouch 100 may then be used within a sterile surgical field. Package antenna 30 is located on pouch 100 and may be a conductive foil or film laminated or adhered to pouch 100, a conductive ink printed onto pouch 100, or a conductive tape or adhesive adhered to pouch 100. Pouch 100 may be packaged with IMD 10 or provided as a separate item available for use during telemetry operations prior to IMD implantation.

If telemetry operations are needed outside the implanted environment, IMD 10 may be inserted into pouch 100 as indicated by arrow 102. Package antenna 30 is shown as a monopole antenna wherein one end 32 is positioned on pouch 100 such that is will be located in close proximity to IMD RF antenna 28 when IMD 10 is fully inserted into pouch 100 thereby establishing a capacitive coupling between end 32 and IMD RF antenna 28.

Figure 7:
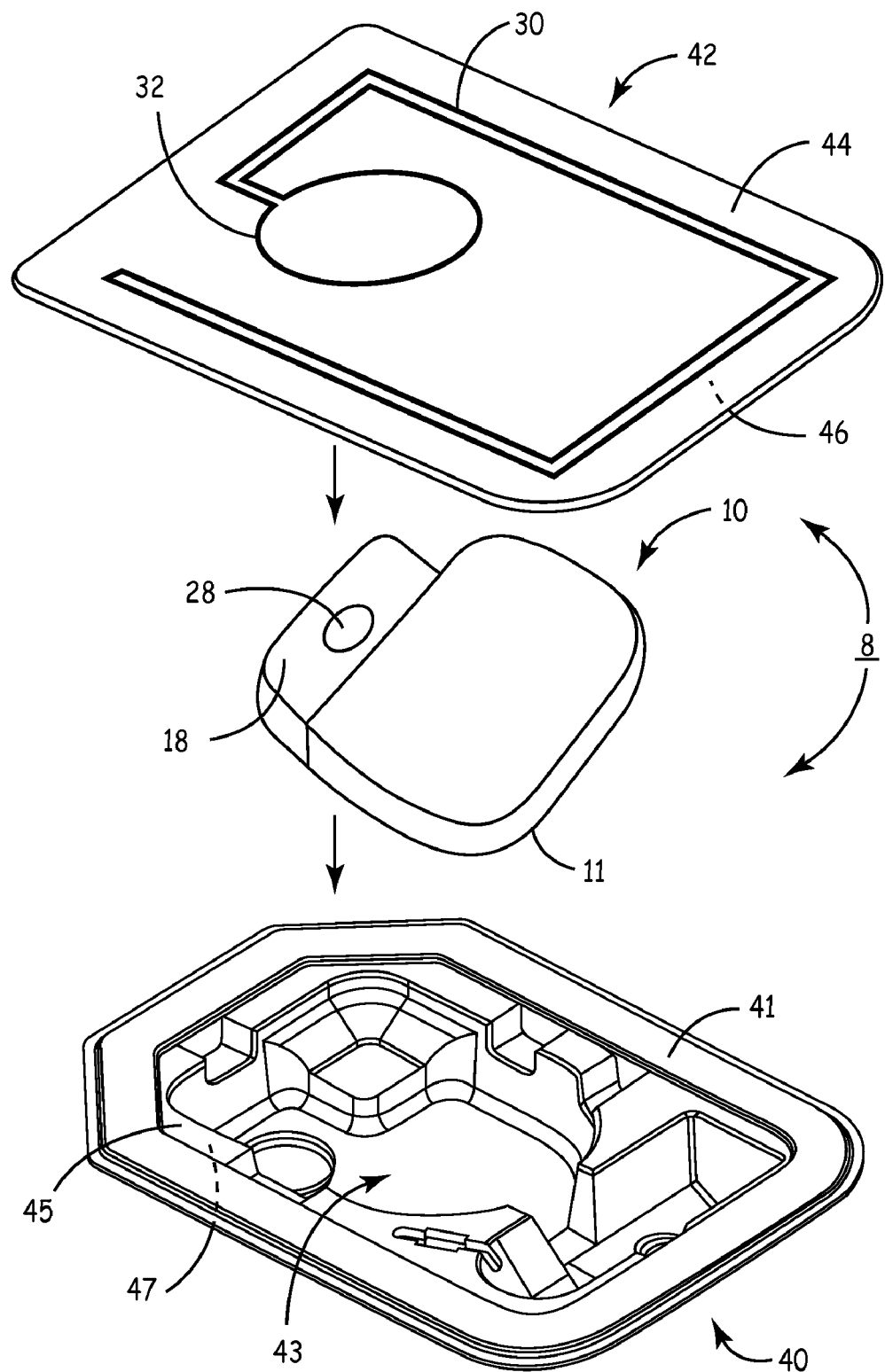
FIG. 7 is an illustration of a package antenna manufactured as a part of a packaging tray assembly.

FIGS. 7 through 14 are illustrations of various embodiments of a package antenna wherein the package antenna is manufactured as part of packaging tray assembly in which the IMD is packaged. In FIG. 7, a packaging tray assembly 8 is shown including a packaging tray 40 and a tray lid 42. Packaging tray assembly 8 is fabricated through thermoforming, injection molding or other appropriate processing of a material that withstands sterilization procedures used to sterilize an IMD 10 contained therein. Packaging tray 40 and tray lid 42 are commonly fabricated from high-density polyethylene. Packaging tray 40 includes a tray seal area 41 that becomes sealed to tray lid 42 during packaging procedures.

Packaging tray 40 includes an inner surface 45 and an outer surface 47 and is formed to provide various cavities and recesses in which to place IMD 10 and any other accessories or tools packaged with IMD 10 for use during implantation of IMD 10. Specifically, packaging tray 40 includes an IMD cavity 43 in which IMD 10 is laid during a packaging procedure. IMD cavity 43 is typically formed to match and substantially mate with the contours of the IMD housing 11 and connector block 18 such that IMD 10 is maintained in a stable position during shipping and handling.

During a packaging procedure, IMD 10 and any other accessories are placed in the appropriate cavities of packaging tray 40, after which tray lid 42 is placed over tray 40 and sealed to sealing area 41. Tray 40 may then be sterilized and placed in any desired outer packaging.

In the embodiment shown in FIG. 7, package antenna 30 is located on tray lid 42 and is a monopole antenna having coupling end 32 positioned so as to establish capacitive coupling to IMD RF antenna 28 when tray lid 42 is placed over tray 40 containing IMD 10. Package antenna 30 may be located on either the outer surface 44 or inner surface 46 of tray lid 42.

The inner surface 46 of tray lid 42 may be coated with adhesive for sealing lid 42 to tray 40. Package antenna 30 may be applied to inner surface 46 as a foil, film, tape, or ink prior to adhesive application to inner surface 46. Alternatively, package antenna 30 may be printed onto inner surface 46 using a conductive ink after applying the adhesive. In yet another embodiment, package antenna 30 may be printed onto inner surface 46 or tray sealing area 41 using a conductive adhesive that also serves to seal tray lid 42 to packaging tray 40.

Package antenna 30 may be continuous as shown in FIG. 7 but could also be provided as a discontinuous antenna having portions on either or both inner and outer surfaces 46 and 44. For example, a portion of package antenna 30 may be located on the outer surface 44 with another portion located on inner surface 46. The outer surface portion and inner surface portion would be located relative to one another to establish capacitive coupling between the two portions creating a continuous antenna for energy transmission.

Figure 8:
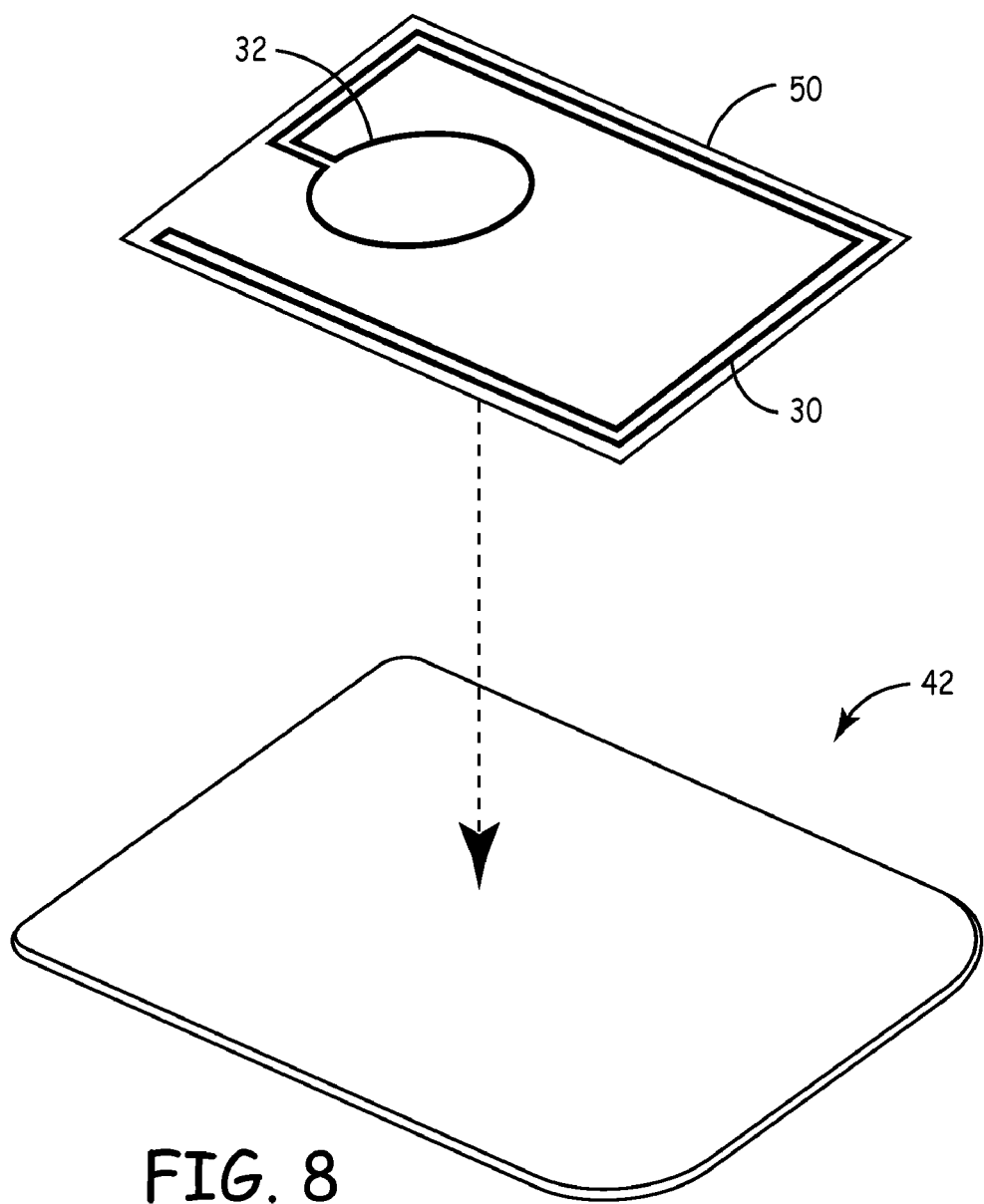
FIG. 8 is an illustration of a package antenna that has been fabricated on or applied to a substrate that can be applied to a surface of a packaging tray assembly.

FIG. 8 is an illustration of a package antenna 30 that has been fabricated on or applied to a substrate 50. Substrate 50 may then be applied to tray lid 42 using an appropriate method such as application of an adhesive, lamination, or other processing in order to fixedly attach substrate 50 to tray lid 42. Substrate 50 could be applied to either the inner or outer surface of tray lid 42. Substrate 50 is positioned on lid 42 such that end 32 of antenna 30 will be located near and capacitively coupled to an IMD RF antenna once tray lid 42 is placed over an associated packaging tray containing an IMD as described above.

Figure 9:
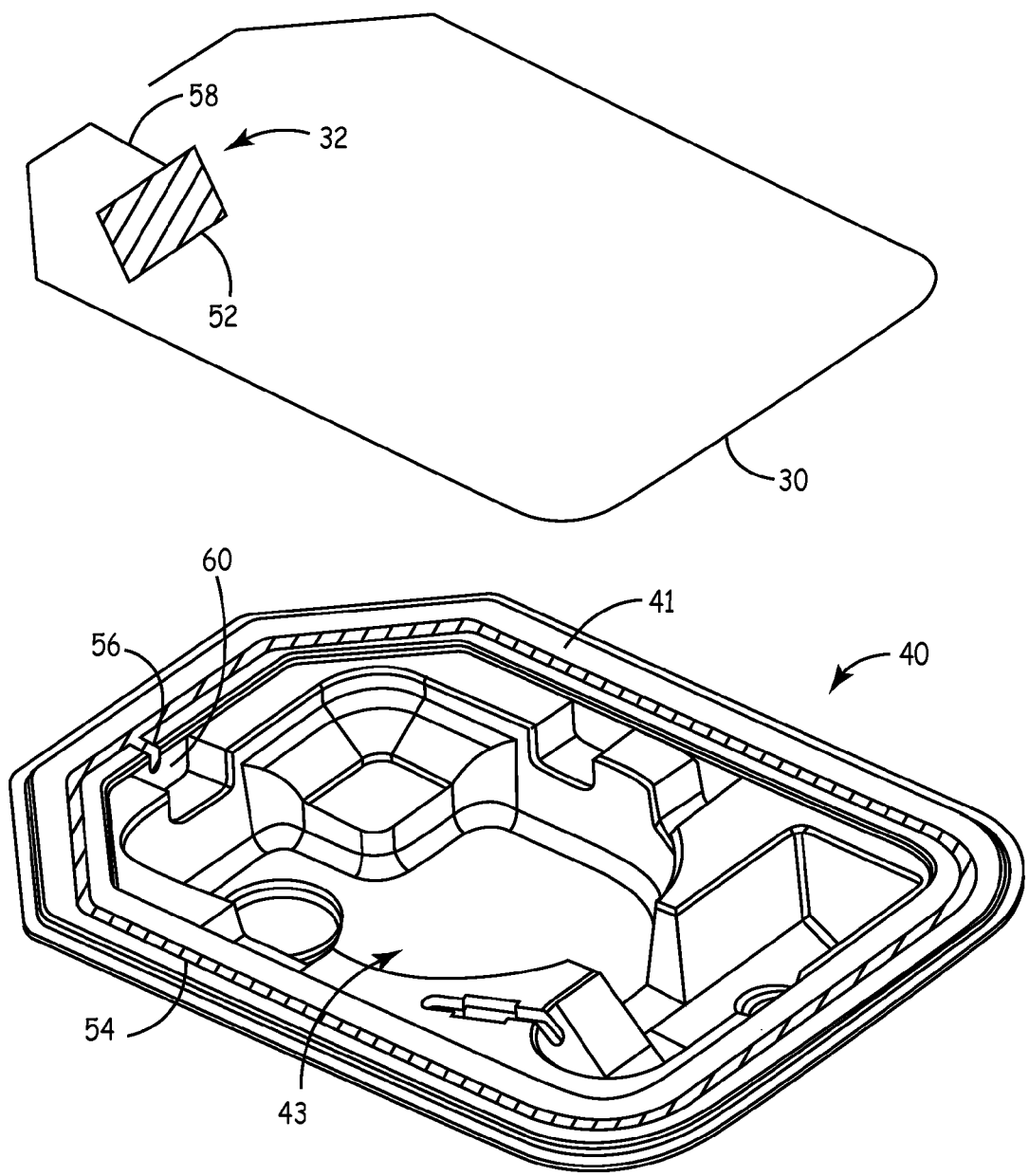
FIG. 9 is an illustration of a package antenna provided in the form of a wire antenna that may be placed within a packaging tray.

FIG. 9 is an illustration of a package antenna 30 provided in the form of a wire antenna that may be placed within packaging tray 40. Packaging tray 40 may be formed with a recess 54 sized for receiving package antenna 30. In this example, recess 54 is formed in the tray seal area 41, which becomes sealed to a tray lid after placing an IMD into IMD cavity 43 and package antenna 30 into recess 54. At end 32, package antenna 30 is provided with a coupling member 52, which may be formed from a conductive tape, foil or film. Coupling member 52 is positioned within packaging tray 40 such that after an IMD is placed in tray 42 the coupling member 52 is located near the IMD RF antenna, and a capacitive coupling between package antenna 30 and the IMD RF antenna is established. In the particular configuration shown in FIG. 9, a portion 58 of package antenna 30 near end 32 extends through a groove 56 provided on packaging tray 40 such that coupling member 52 will rest in a cavity 60 that will be adjacent to the connector block of an IMD placed in IMD cavity 43. Coupling member 52 will thus be positioned close to an IMD RF antenna located in the connector block and thereby establish capacitive coupling between package antenna 30 and the IMD RF antenna.

Figure 10:
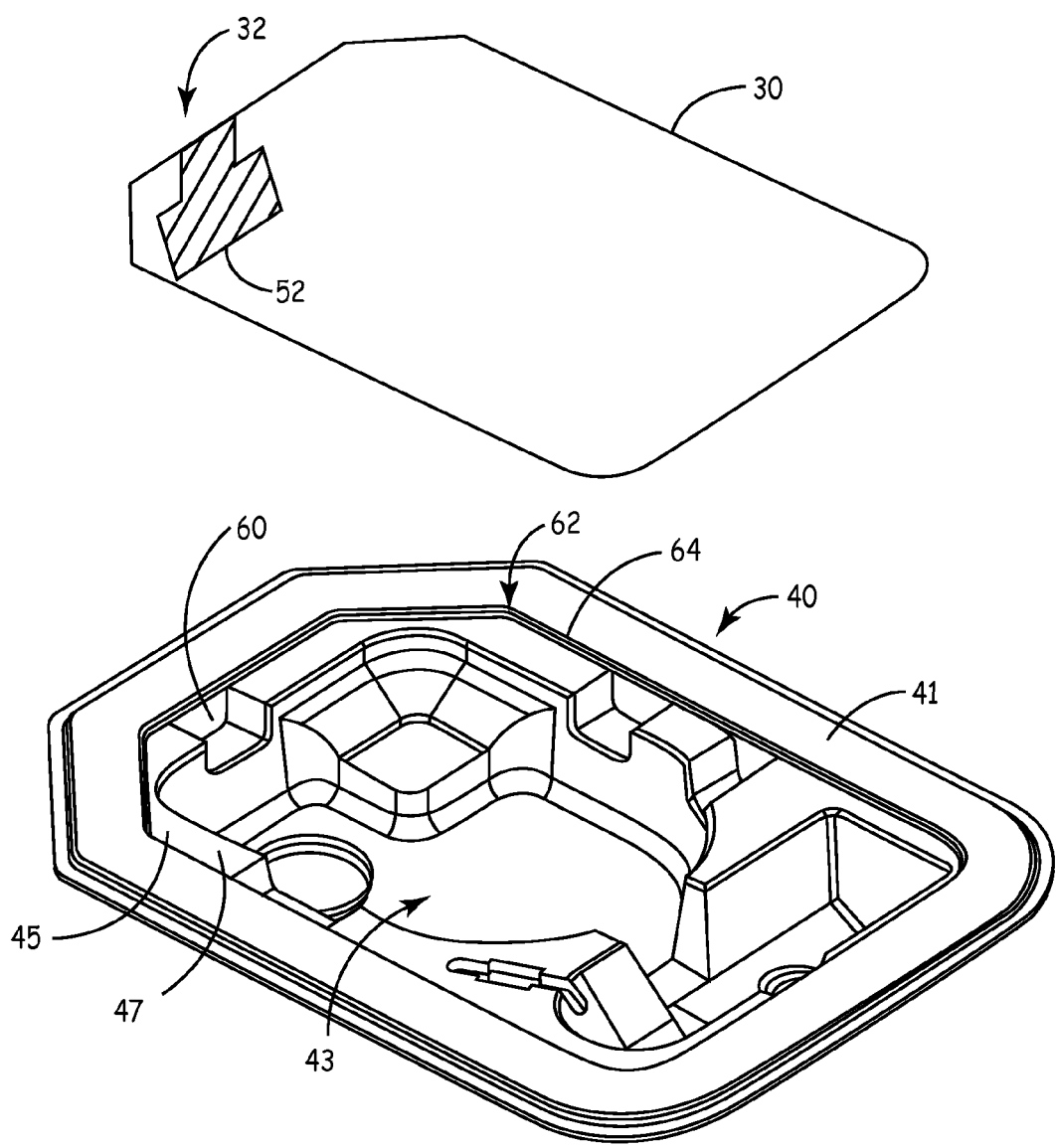
FIG. 10 is an illustration of an alternative embodiment of a package antenna provided as a wire antenna that may be placed within a packaging tray.

FIG. 10 is an illustration of an alternative embodiment of a package antenna 30 provided as a wire antenna that may be placed within a packaging tray 40. Package antenna 30 may be placed within packaging tray 40 such that antenna 30 rests along the outer periphery 62 of the inner surface 45 of tray 40. An antenna recess 64 may be formed along the periphery 62 of the inner tray surface 45 for receiving package antenna 30 and preventing it from shifting during shipping and handling.

Package antenna 30 is provided with coupling member 52 at antenna end 32 for establishing capacitive coupling with an IMD RF antenna after the IMD is placed in IMD cavity 43 and package antenna 30 is placed in antenna recess 64. Coupling member 52 may rest in cavity 60 of tray 40 such that it is close enough to the IMD RF antenna to establish capacitive coupling. Coupling member 52 may be formed from conductive tape, foil or film and may be adhered to at least a portion of the inner surface of cavity 60 such that coupling member 52 is held in a stable position with respect to an IMD placed in tray 40.

Figure 11:
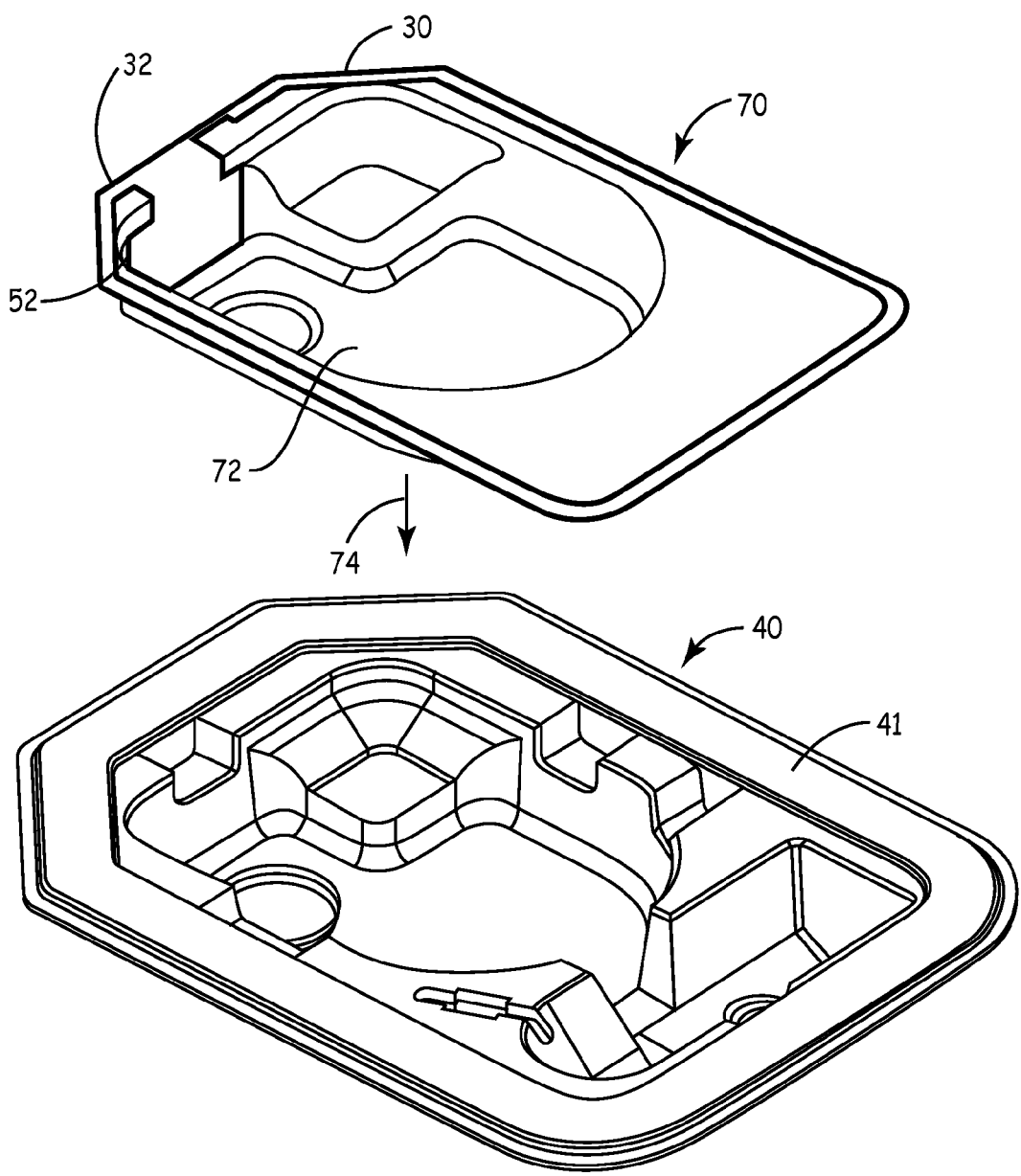
FIG. 11 is an illustration of a package antenna located on an antenna tray adapted for placement inside a packaging tray.

FIG. 11 is an illustration of a package antenna 30 located on an antenna tray 70 adapted for placement inside a packaging tray 40. In accordance with the present invention, a packaging tray assembly including a packaging tray 40 and tray lid (see FIG. 7), may further include antenna tray 70 for accommodating a package antenna. Antenna tray 70 may be fabricated using similar methods used for fabrication of packaging tray 40 such as thermoforming or injection molding. Antenna tray 70 can be formed from the same material as packaging tray 70 or any suitable material that can withstand sterilization procedures used for sterilizing an IMD to be contained in packaging tray 40. Package antenna 30 is contained by, or attached to, antenna tray 70. Package antenna 30 may be a wire antenna placed in a recess provided on antenna tray 70 or formed from conductive tape, ink, foil or film applied to antenna tray 70.

During packaging procedures, an IMD is placed in an IMD cavity 72 formed in antenna tray 70 to approximately match the contours of the IMD. Package antenna 30 is provided with coupling member 52 at end 32 that will be located in close proximity to the IMD RF antenna once the IMD is laid in antenna tray 70. Antenna tray 70 is then laid in packaging tray 40 as indicated by arrow 74. A tray lid may then be laid over and sealed to packaging tray 40 along sealing area 41 as described previously. Package antenna 30 is thus maintained in a stable position relative to the IMD contained in antenna tray 70 to allow efficient, reliable telemetry transmission as long as the IMD is remains in antenna tray 70.

Figure 12:
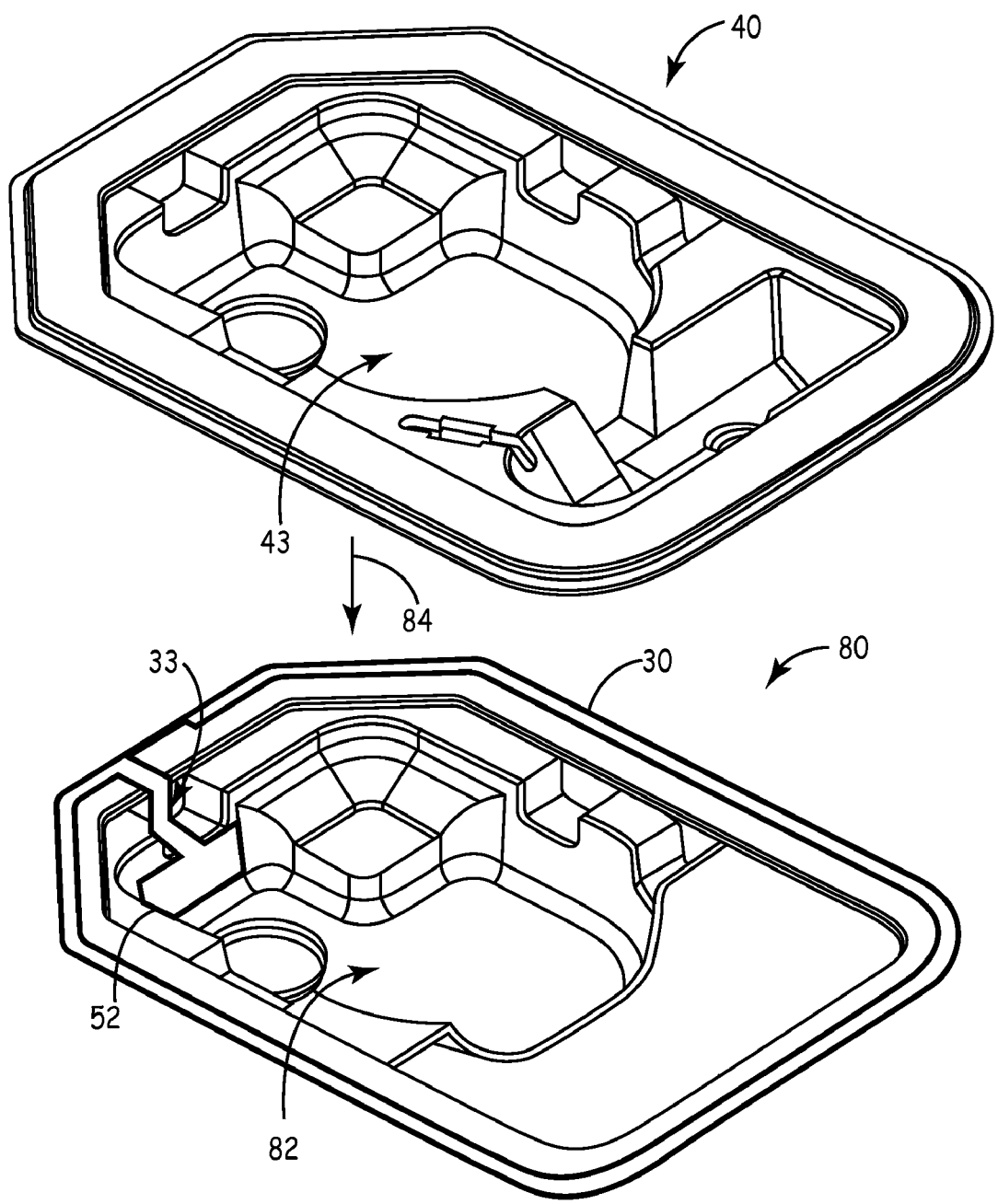
FIG. 12 is an illustration of an alternative embodiment of an antenna tray used for carrying a package antenna.

FIG. 12 is an illustration of an alternative embodiment of an antenna tray 80 used for carrying a package antenna 30. In this embodiment, package antenna 30 is contained in or stably attached to antenna tray 80, as described above, however antenna tray 80 is sized and formed such that packaging tray 40 may be placed into antenna tray 80. During a packaging procedure, an IMD is laid into IMD cavity 43 formed in packaging tray 40. Packaging tray 40 may then be sealed shut using a tray lid as described previously. Packaging tray 40 is then placed into packaging tray cavity 82 formed in antenna tray 80 as indicated by arrow 84. As a result, coupling member 52 provided at end 32 of package antenna 30 is located within range of the IMD RF antenna for establishing capacitive coupling. The antenna tray 80, containing packaging tray 40, may then be sealed closed with an associated lid if desired and placed in any desired outer packaging materials.

Figure 13:
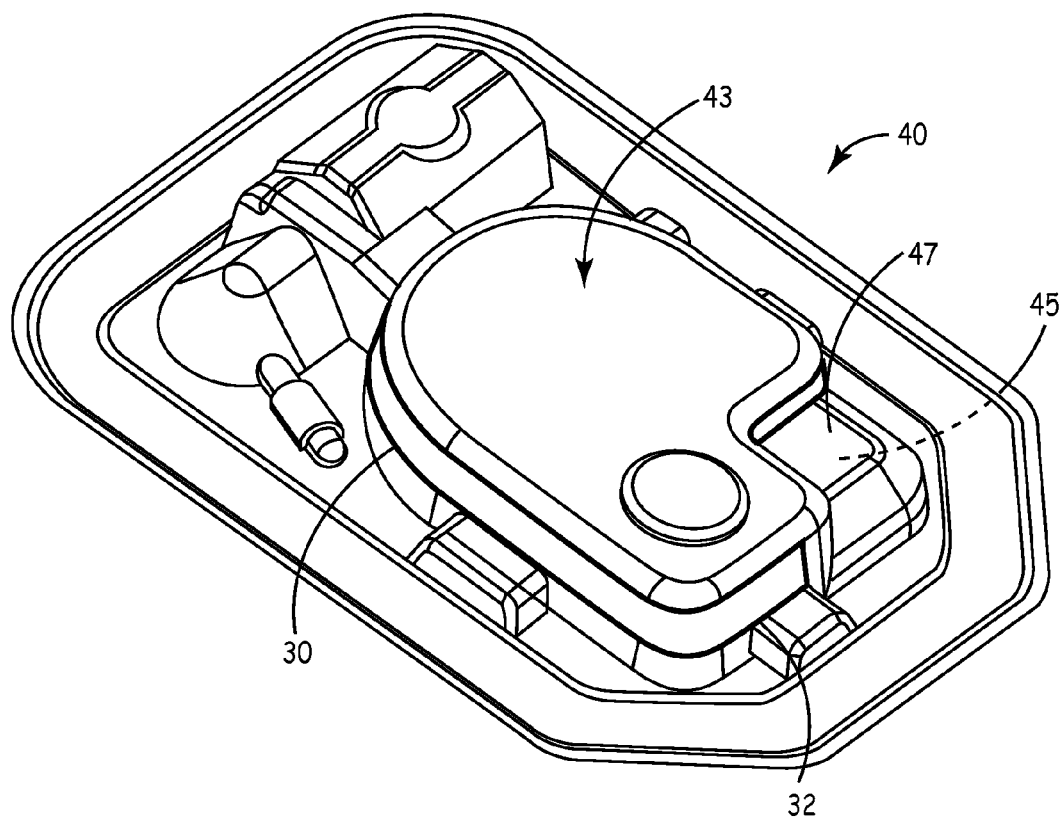
FIG. 13 is an illustration of a package antenna provided on the outer surface of a packaging tray.

FIG. 13 is an illustration of a package antenna 30 provided on the outer surface 47 of a packaging tray 40. Package antenna 30 is shown applied to the vertical outer surface of the perimeter of IMD cavity 43. Package antenna end 32 is located such that capacitive coupling to an IMD RF antenna will be established when the IMD is placed in IMD cavity 43.

Figure 14:
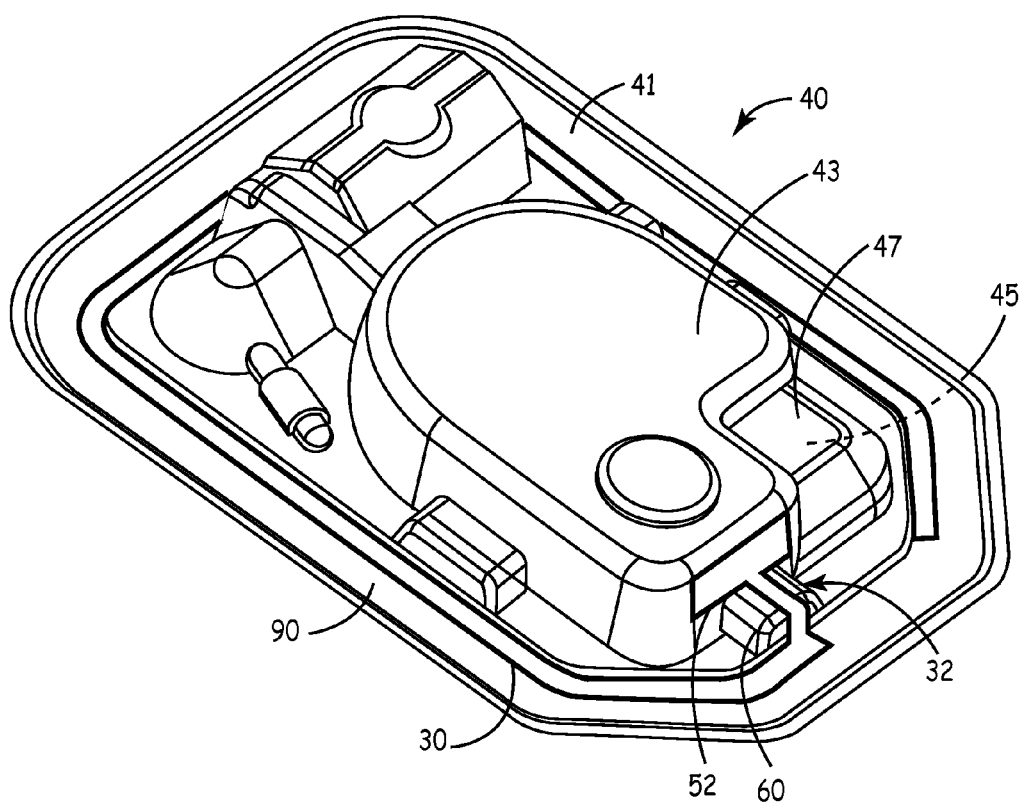
FIG. 14 is an illustration of an alternative embodiment of a package antenna provided on the outer surface of a packaging tray.

FIG. 14 is an illustration of an alternative embodiment of a package antenna 30 provided on the outer surface 47 of packaging tray 40. In this example, antenna 30 is located along the outer surface of a flange 90 that forms, on its inner surface, sealing area 41 for interfacing with a tray lid. Package antenna 30 is provided with coupling member 52 at end 32. Coupling member 52 is located on the outer surface 47 of IMD cavity 43 such that when an IMD is placed in cavity 43 capacitive coupling between member 52 and the IMD RF antenna is established.

As can be seen by the illustrations shown in FIGS. 7 through 14, numerous variations may be conceived for manufacturing a package antenna as a part of a packaging tray assembly used for containing the IMD during sterilization, shipping and handling. As shown by the above examples, a package antenna may be printed or attached to the inner or outer surfaces of a packaging tray or the associated tray lid or provided on an additional antenna tray. A variety of shapes and sizes of packaging trays will exist for use with different types of IMDs produced by different manufacturers. As such, numerous possible configurations will exist which enable a package antenna manufactured as a part of a packaging tray assembly to effectively extend the length of an IMD RF antenna as long as the IMD is contained in the packaging assembly. The telemetry system is improved for use outside the implanted environment by taking advantage of the additional space available for an antenna in or on the packaging material.

A package antenna may alternatively be provided as a separate, portable device. One example of a separate portable package antenna was described previously in conjunction with FIG. 6 wherein a package antenna is fabricated as part of a pouch in which an IMD may be placed. A separate, portable package antenna may alternatively be fabricated as part of an overlay that may be positioned over a non-implanted IMD to couple the package antenna to the IMD RF antenna.

Figure 15:
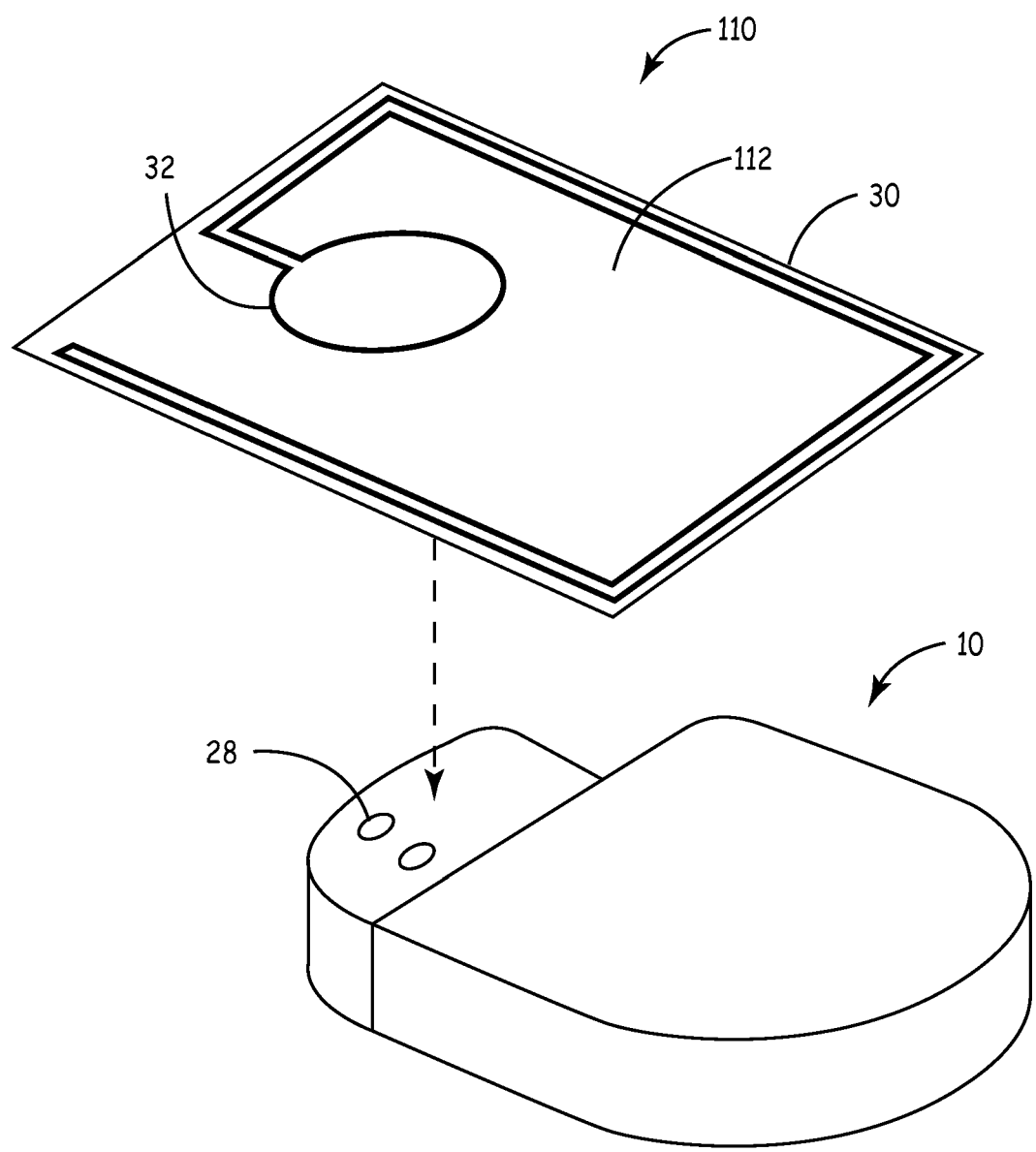
FIG. 15 is an illustration of a package antenna overlay.

FIG. 15 is an illustration of a package antenna overlay 110. Overlay 110 includes a substrate 112 and package antenna 30 fabricated onto or attached to substrate 112. Substrate 112 may be formed as a flat sheet in a simple embodiment and may be provided with markings or other indicators for guiding the alignment of overlay 110 relative to IMD 10 such that package antenna end 32 becomes capacitively coupled to IMD RF antenna 28. In alternative embodiments, substrate 112 may be formed in a contoured two-dimensional or three-dimensional shape that matches at least a portion of the contours of IMD 10 in order to promote proper positioning of overlay 110 relative to IMD 10.

Package antenna 30 may be fabricated from conductive wire, film, foil, ink, tape or other conductive material and placed on substrate 112 by lamination, printing, adhesion or other appropriate manufacturing methods. Overlay 110 may be packaged with an IMD or separately. Overlay 110 preferably withstands sterilization methods such that overlay 110 may be used within a sterile surgical field.

In the various examples shown above, package antenna 30 is illustrated as a continuous, monopole antenna having one end coupled to the IMD RF antenna. In alternative embodiments, a package antenna may be embodied as a discontinuous antenna, a microstrip patch antenna, a slot antenna, a dipole antenna, a loop antenna, or any other antenna configurations known for use in transmitting and receiving wireless communication signals.

Figure 16:
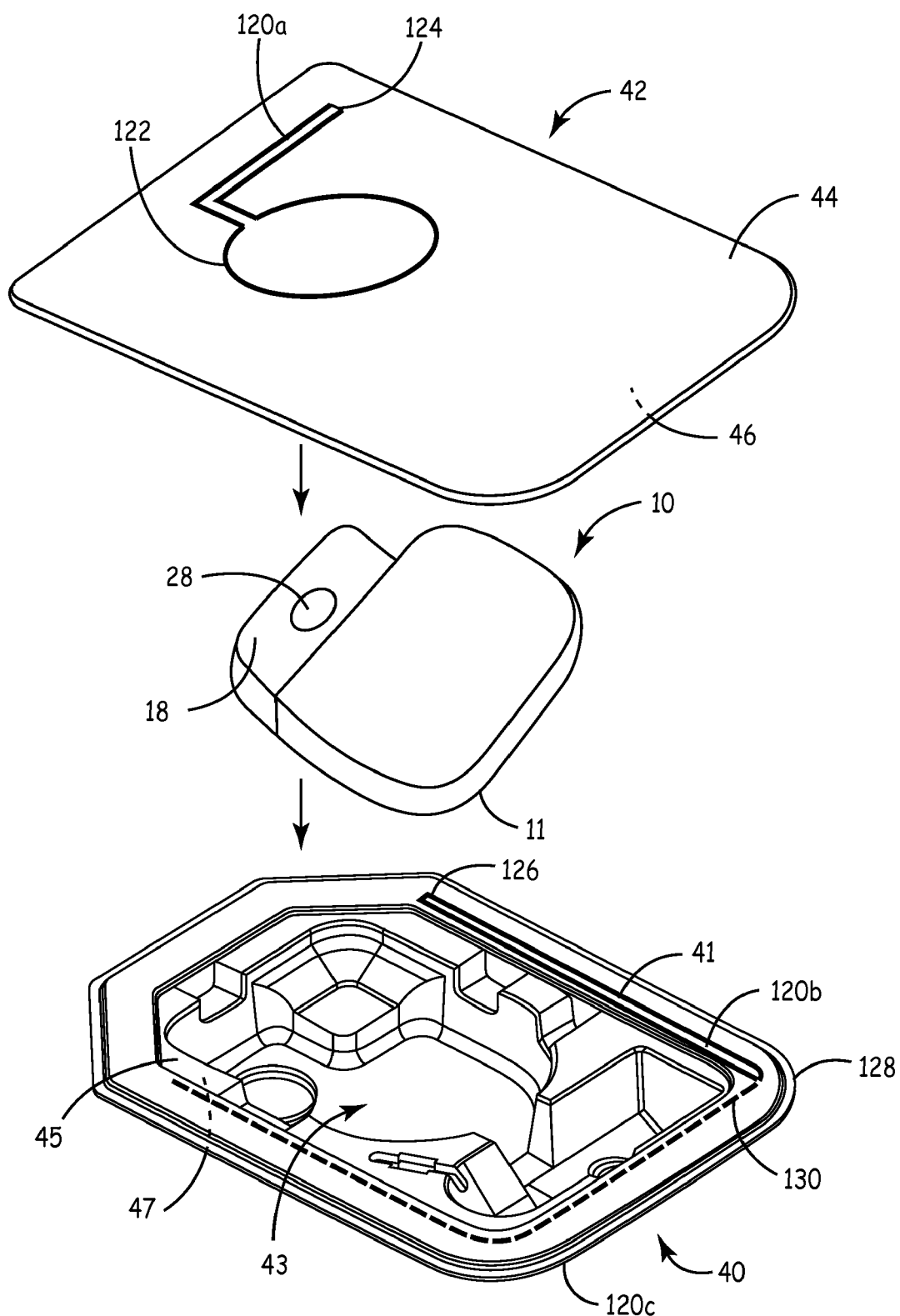
FIG. 16 is an illustration of one example of a discontinuous package antenna.

FIG. 16 is an illustration of one example of a discontinuous package antenna. A discontinuous package antenna may have portions fabricated onto different elements or surfaces of a packaging assembly, an overlay and/or a pouch. In the example shown in FIG. 16, a package antenna is formed by portions 120a, 120b and 120c located, respectively, on tray lid 42, sealing area 41 of packaging tray 40, and outer surface 47 of packaging tray 40. After placing IMD 10 in IMD cavity 43 and sealing tray lid 42 to packaging tray 40, portion 120a will be capacitively coupled at end 122 to IMD RF antenna 28. Portion 120a will be capacitively coupled at end 124 to end 126 of portion 120b. Likewise, portion 120b will be capacitively coupled at end 128 to end 130 of portion 120c.

While discontinuous package antennas will be functional in an IMD telemetry system, discontinuous antennas will generally be less efficient than continuous antennas. However, depending on the packaging materials available or other design considerations, other advantages or reasons may exist for providing a discontinuous package antenna. For example, a discontinuous antenna may be desirable in order to extend the package antenna length by applying portions of the discontinuous package antenna to different substrates within a packaging assembly.

Figure 17:
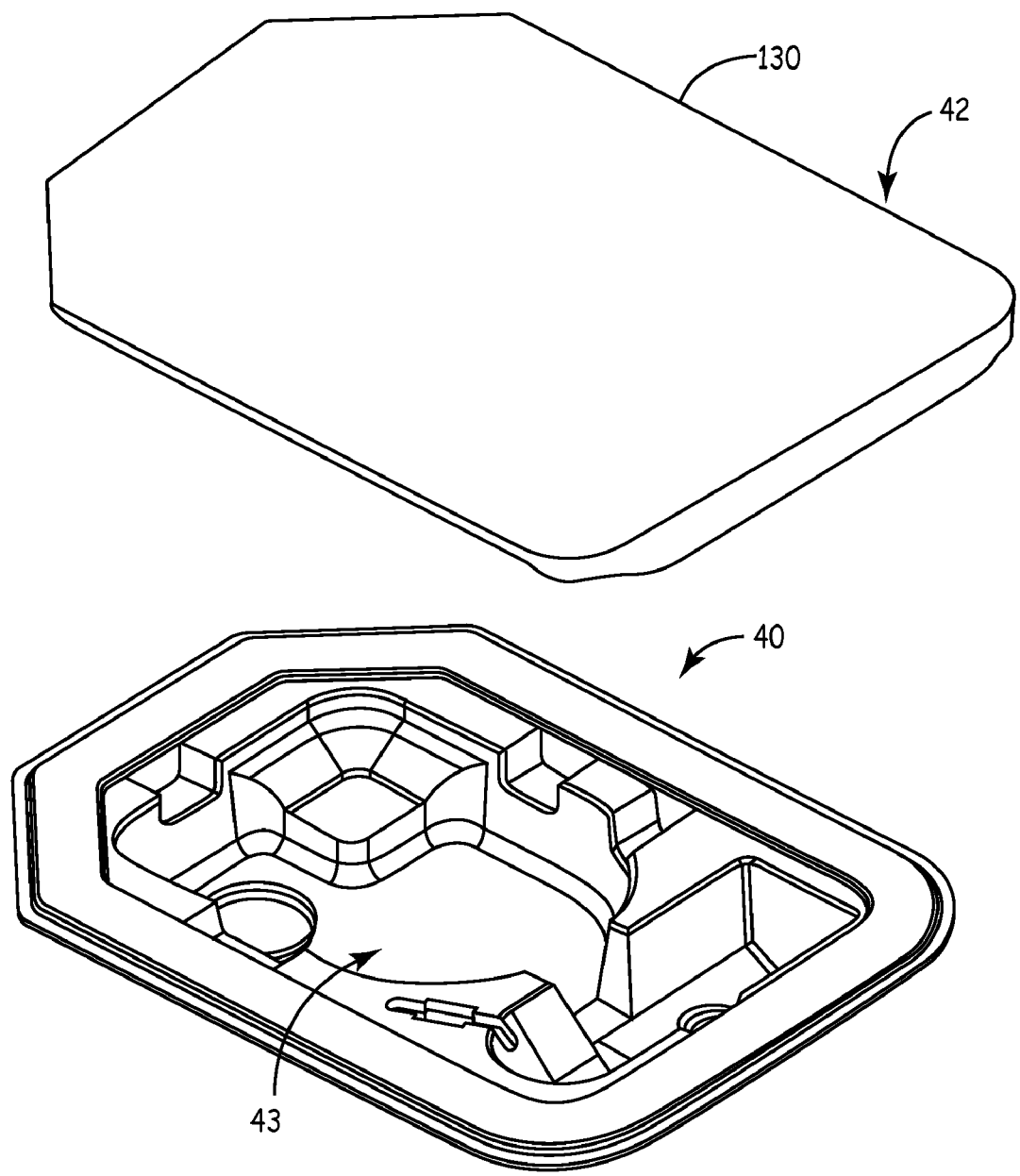
FIG. 17 is an illustration of a microstrip patch package antenna manufactured on the surface of a packaging tray assembly.

FIG. 17 is an illustration of a microstrip patch antenna that may be embodied as a package antenna. A microstrip patch package antenna 130 may be formed on a packaging tray lid 42 by printing, gluing or otherwise adhering a conductive material onto tray lid 42 leaving no open areas or voids. When tray lid 42 is sealed to packaging tray 40 containing an IMD in IMD cavity 43, microstrip patch package antenna 130 will be capacitively coupled to the IMD RF antenna. In alternative embodiments, a microstrip patch package antenna may be formed on another surface of a packaging tray assembly, on a substrate material applied to tray lid 42 or packaging tray 40 or on an overlay or pouch.

A microstrip patch antenna generally includes a conducting patch positioned above a ground plane. A package antenna embodied as a microstrip patch as shown in FIG. 17 may utilize a metal surgical table as the ground plane. The microstrip patch package antenna 130 will be coupled to the IMD RF antenna, and the IMD housing will be coupled to the surgical table acting as the ground plane.

Figure 18:
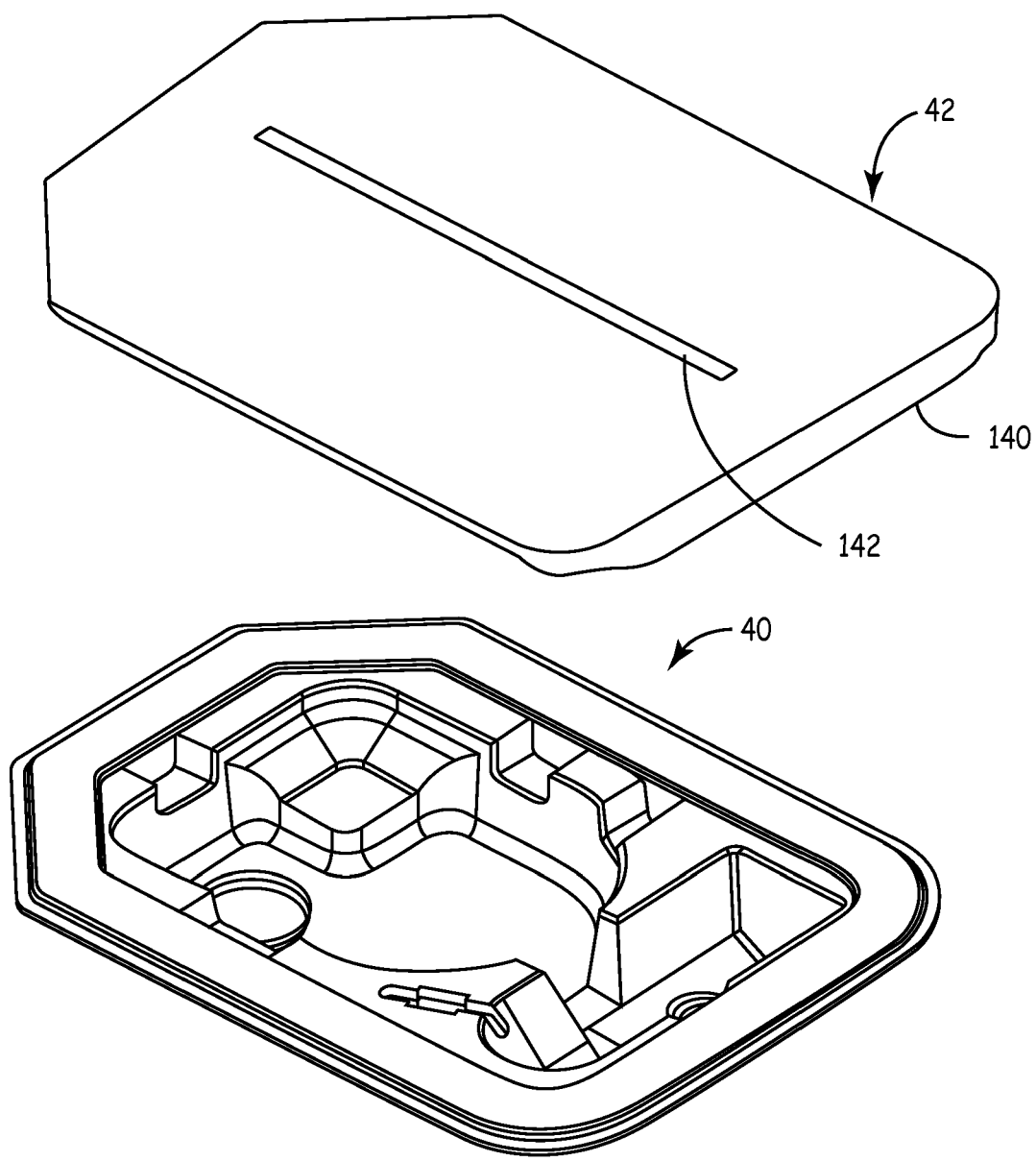
FIG. 18 is an illustration of a slot package antenna.

FIG. 18 is an illustration of a slot package antenna. In this embodiment, tray lid 42 is printed with a conductive material leaving a slot-shaped void 142 to form slot package antenna 140. A slot package antenna may alternatively be provided on another surface of a packaging tray assembly, a pouch, an overlay, or a substrate to be adhered to a packaging tray surface.

Figure 19:
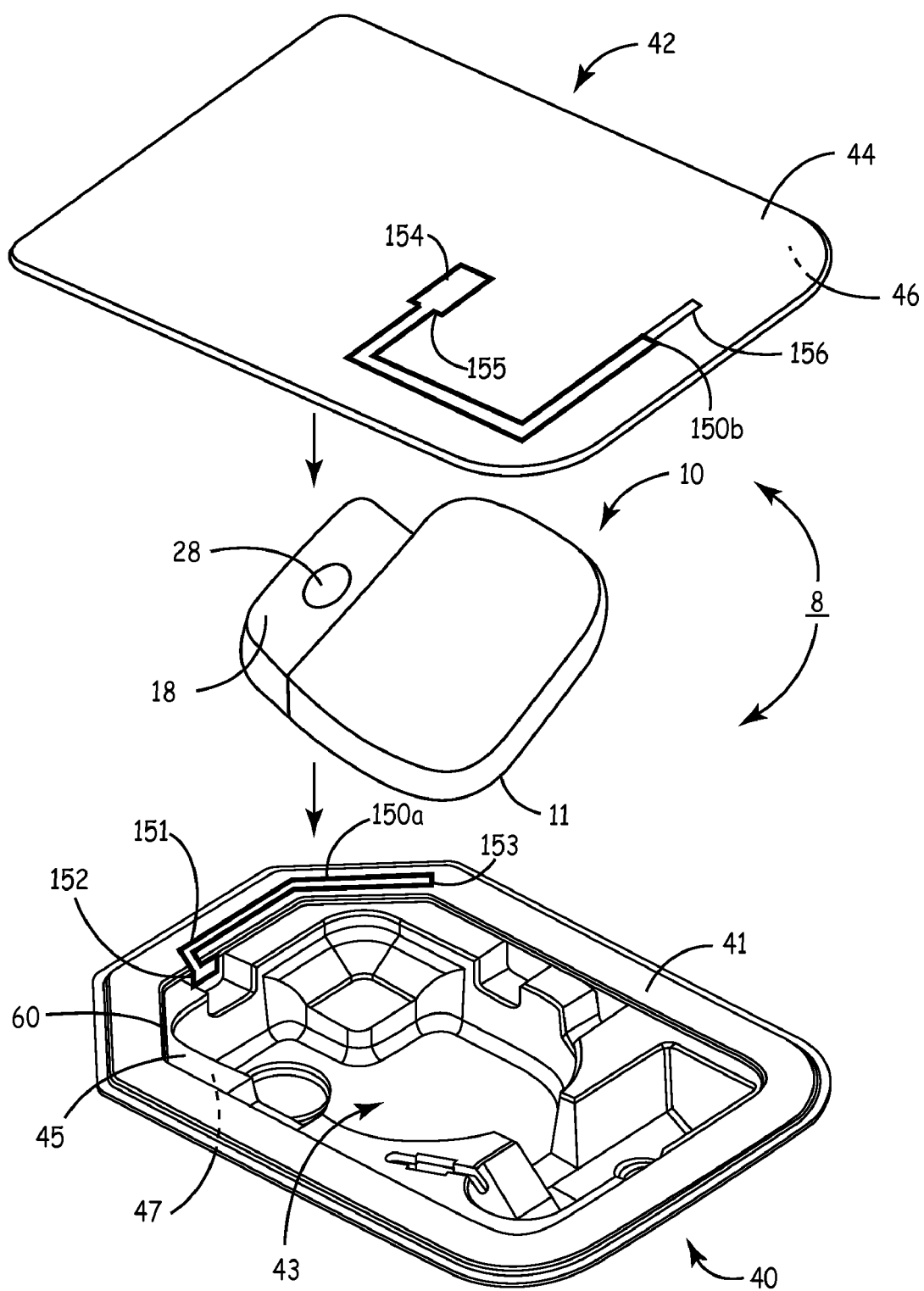
FIG. 19 is an illustration of one embodiment of a dipole package antenna.

FIG. 19 is an illustration of one embodiment of a dipole package antenna. A dipole package antenna is formed of two portions 150a and 150b. A first portion 150a of the dipole package antenna is shown to be located on sealing area 41 of packaging tray 40. A coupling member 152 is provided at end 151 for coupling to IMD RF antenna 28 when IMD 10 is placed in IMD cavity 43. Portion 150a may be located on the inner surface 45 or outer surface 47 of tray 40.

A second portion 150b of the dipole package antenna is shown located on tray lid 42. Portion 150b may be located on either the inner surface 46 or outer surface 44 of lid 42. Portion 150b includes a coupling member 154 at end 155 for capacitive coupling to IMD housing 11 when IMD 10 is placed in IMD cavity 43 and tray lid 42 is placed over packaging tray 40. Thus a dipole package antenna is formed by portions 150a and 150b wherein portion 150a is coupled to IMD RF antenna at end 151 and forms one antenna pole at end 153. Portion 150b is coupled to IMD housing 11 (can), which serves as a ground, at end 155 and forms a second pole at end 156. In other embodiments, a dipole package antenna may be formed on a packaging tray assembly, a pouch or an overlay or any combination of these wherein one pole is located on one surface and the second pole is located on the same or a different surface some distance from the first pole.

Figure 20:
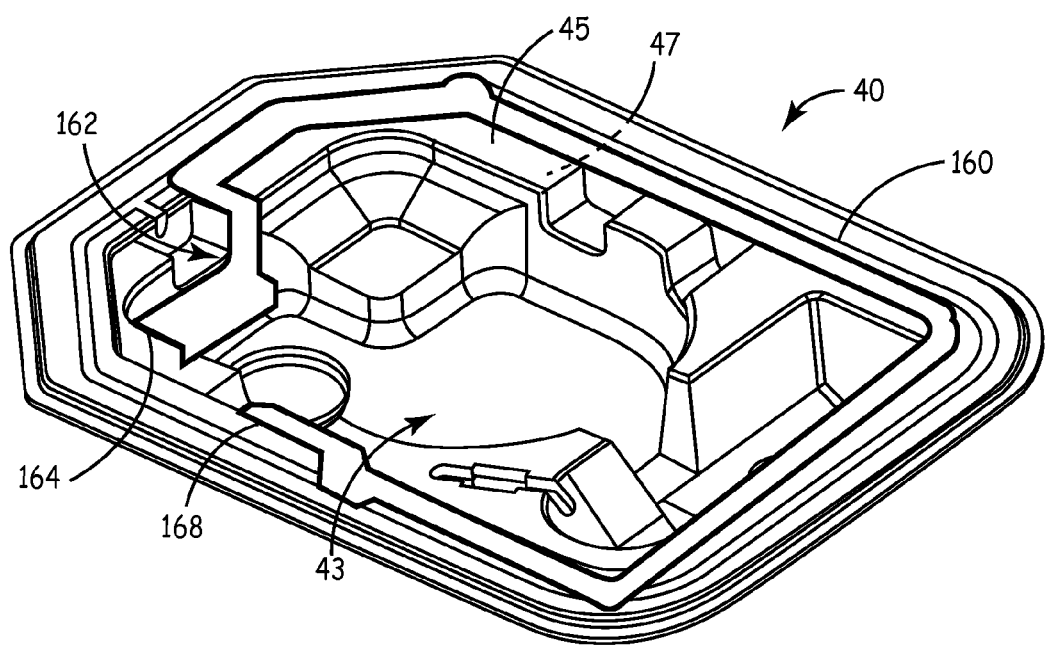
FIG. 20 is an illustration of one embodiment of a loop package antenna.

FIG. 20 is an illustration of one embodiment of a loop package antenna. A loop package antenna 160 is shown located on packaging tray 40. A coupling member 164 is provided at coupling end 162 for coupling to the RF antenna of an IMD when it is placed in IMD cavity 43. A second coupling member 168 is provided at end 166 for coupling to the IMD housing, which serves as a ground. Loop package antenna 160 may be located on the inner surface 45 or outer surface 47 of packaging tray 40. In other embodiments, a loop package antenna may be located on another surface of a packaging assembly, a pouch, or an overlay.

Figure 21A:
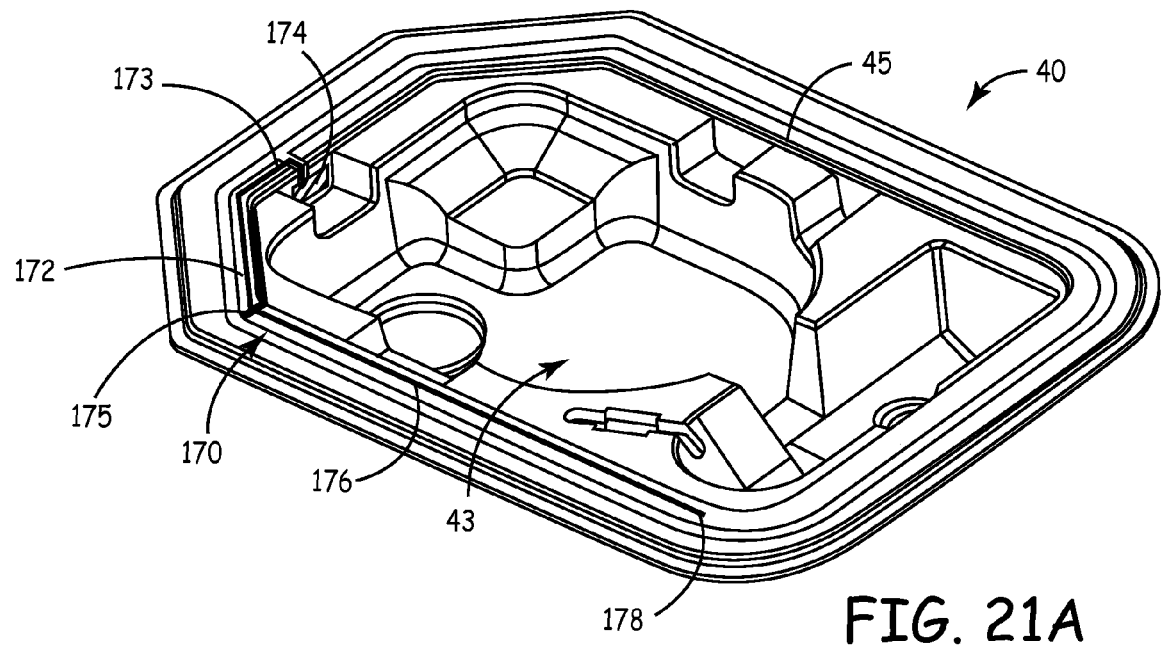
FIG. 21A is an illustration of one embodiment of a folding package antenna.

FIG. 21A is an illustration of one embodiment of a folding package antenna. In the various embodiments of monopole and dipole package antennas described above, the package antenna is printed or attached to a selected surface or substrate and is immovable with respect to that surface. A package antenna may alternatively be provided as a movable antenna wherein the end that is coupled to an IMD antenna or ground remains at a fixed location and the other end, which forms a pole, is movable relative to the coupled end.

For example, a movable monopole antenna may be provided as a folding antenna 170 as shown in FIG. 21A. Folding antenna 170 includes an immovable portion 172 and a movable portion 176 joined by a hinge 175. Immovable portion 172 is provided with a coupling member 174 at coupling end 173. Immovable portion 172 is located on the inner surface 45 of tray 40 such that coupling member 174 can be capacitively or directly coupled to an IMD RF antenna when the IMD is placed in IMD cavity 43.

Movable portion 176 extends from hinge 175 along inner surface 45 of packaging tray 40 forming a pole at end 178. When a telemetry operation is required, movable portion 176 may be rotated on hinge 175 as needed to adjust the spatial location of pole end 178 in order to establish and maintain good signal strength. An associated tray lid would be removed to allow movement of movable portion 176, but the packaged IMD would remain in IMD cavity 43.

Figure 21B:
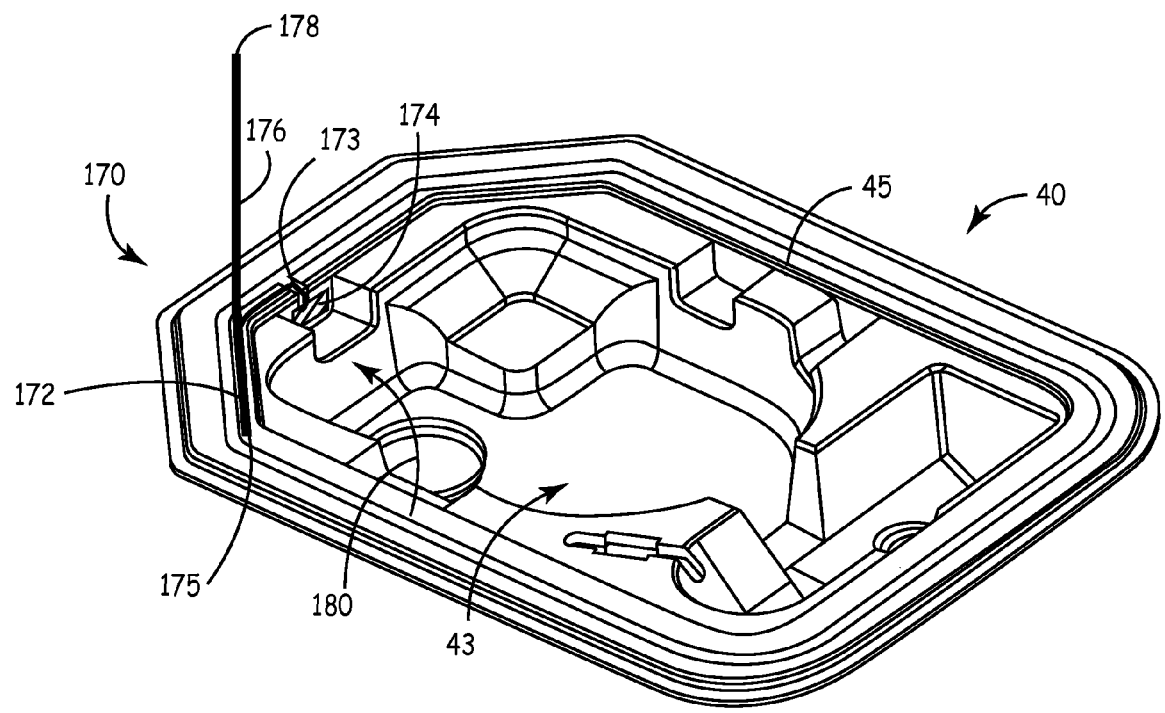
FIG. 21B is an illustration of the folding package antenna shown in FIG. 21A wherein a movable portion of the folding antenna is shown rotated relative to a hinge.

FIG. 21B is an illustration of folding package antenna 170 with movable portion 178 rotated in a direction indicated by arrow 180 to an approximately vertical position relative to immovable portion 172. The movable portion 178 of antenna 170 is shown to rotate on hinge 175 in a plane approximately vertical to the plane of immovable portion 172. A hinge or other mechanism provided to allow rotation of a movable portion of a folding antenna about the hinge may be configured to allow rotation of the movable portion in the same or a different plane than the plane of the immovable portion. Other mechanisms may be substituted for hinge 172 to allow movement of movable portion 176. For example, a movable antenna may be provided as a telescoping antenna.

In other embodiments of a movable package antenna, the antenna may be located on a tray lid or other portion of a packaging assembly, on a pouch or overlay. A movable package antenna may be discontinuous such that an immovable portion and a movable portion are not physically connected but are capacitively coupled so as to provide continuous energy transmission. A discontinuous movable package antenna would allow an immovable portion coupled to the IMD antenna to be located, for example on an inner surface of a packaging assembly containing the IMD and the movable portion to be located on an outer surface of a packaging assembly or on an accessory pouch or overlay to allow movement of the movable portion without opening the packaging assembly.

A wireless communication system that includes a package antenna has thus been described which promotes efficient and reliable telemetry communication between an IMD and a programmer or monitor when the IMD is outside the implanted environment. Detailed descriptions provided herein are intended to be illustrative of methods for practicing the present invention. It is recognized that numerous variations of a package antenna for use with either implantable or external medical devices may be conceived by one having skill in the art and the benefit of the teachings provided herein. The various embodiments presented herein should, therefore, be considered exemplary, not limiting, with regard to the following claims.

What is claimed is:

1. A wireless communication system, comprising:
   a programmer including an antenna;
   a medical device including an implantable telemetry antenna;
   a substrate; and
   an antenna structure extending along a surface of the substrate in proximity to the medical device and removably coupled to the medical device implantable telemetry antenna for extending the effective length of the implantable telemetry antenna;
   said substrate adapted to position the medical device in proximity to the antenna structure to facilitate the removable coupling of the antenna structure and the implantable telemetry antenna;
   said programmer antenna enabled to wirelessly communicate with said medical device implantable telemetry antenna via said antenna structure.

2. The wireless communication system of claim 1 wherein the antenna structure is adapted to be capacitively coupled to the implantable telemetry antenna.

3. The wireless communication system of claim 1 wherein the antenna structure is adapted to be directly coupled to the implantable telemetry antenna.

4. The wireless communication system of claim 1 wherein the antenna structure includes a configuration to extend the range of communication between the medical device and the programmer.

5. The wireless communication system of claim 1 wherein the antenna structure includes an antenna selected from the group of: a monopole antenna, a dipole antenna, a microstrip patch antenna, a slot antenna, and a loop antenna.

6. The wireless communication system of claim 1, wherein the substrate being adapted for cradling the medical device.

7. A wireless communication architecture, comprising:
   a medical device including an implantable telemetry antenna;
   an antenna structure removably coupled to the medical device implantable telemetry antenna to extend the effective electrical length of said implantable telemetry antenna; and
   a substrate for placement of the antenna structure;
   said medical device being in communication with said antenna structure.

8. The communication architecture of claim 7 wherein the antenna structure includes a first end fixedly attached to the substrate and adapted for removable coupling to the implantable telemetry antenna to enable communication with the medical device and a second end movable relative to the first end.

9. The communication architecture of claim 8 wherein the antenna structure is a folding antenna.

10. The communication architecture of claim 8 wherein the antenna structure is a telescoping antenna.

11. The communication architecture of claim 7 wherein the antenna structure includes a plurality of physically discontinuous portions on at least one of the substrate surfaces.

12. The communication architecture of claim 7 wherein the substrate forms a part of a packaging tray assembly.

13. A wireless communication system, comprising:
   means for extending the range of communication between an implantable telemetry antenna of a medical device and a programmer antenna;
   means for removably positioning the extending means relative to the medical device to removably couple the extending means to the implantable telemetry antenna of the medical device; and
   means for communicating information between implantable telemetry antenna of the medical device and the programmer antenna via the extending means.

14. A wireless communication system, comprising:
   a programmer comprising an antenna;
   a medical device comprising telemetry circuitry;

a medical device implantable antenna coupled to the telemetry circuitry; and
an antenna structure in proximity to the medical device and removably coupled to the medical device implantable antenna to increase the electrical length of said medical device implantable antenna;

said programmer antenna enabled to wirelessly communicate with said medical device implantable antenna via said antenna structure.

* * * * *